US010501563B2

(12) United States Patent
You et al.

(10) Patent No.: US 10,501,563 B2
(45) Date of Patent: Dec. 10, 2019

(54) METHOD OF PREPARING SUPPORTED METALLOCENE CATALYST

(71) Applicant: LG CHEM, LTD., Seoul (KR)

(72) Inventors: Young Suk You, Daejeon (KR); Kyung Jin Cho, Daejeon (KR); Hyuck Ju Kwon, Daejeon (KR); Yi Young Choi, Daejeon (KR); Ki Soo Lee, Daejeon (KR); Eun Kyoung Song, Daejeon (KR); Woo Ri Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 15/566,098

(22) PCT Filed: Jun. 13, 2016

(86) PCT No.: PCT/KR2016/006264
§ 371 (c)(1),
(2) Date: Oct. 12, 2017

(87) PCT Pub. No.: WO2016/204469
PCT Pub. Date: Dec. 22, 2016

(65) Prior Publication Data
US 2018/0094084 A1    Apr. 5, 2018

(30) Foreign Application Priority Data

Jun. 15, 2015  (KR) .................. 10-2015-0084483
Mar. 11, 2016  (KR) .................. 10-2016-0029835

(51) Int. Cl.
| C08F 4/653 | (2006.01) |
| C08F 4/6592 | (2006.01) |
| C08F 210/16 | (2006.01) |
| C08F 2/38 | (2006.01) |
| C08F 4/02 | (2006.01) |
| C08F 10/02 | (2006.01) |
| C08F 10/06 | (2006.01) |
| C08F 10/14 | (2006.01) |
| C08F 110/02 | (2006.01) |
| C07F 7/00 | (2006.01) |
| C08F 4/659 | (2006.01) |
| C08F 2/06 | (2006.01) |

(52) U.S. Cl.
CPC ............. *C08F 4/6592* (2013.01); *C08F 2/38* (2013.01); *C08F 4/02* (2013.01); *C08F 10/02* (2013.01); *C08F 10/06* (2013.01); *C08F 10/14* (2013.01); *C08F 110/02* (2013.01); *C07F 7/00* (2013.01); *C08F 2/06* (2013.01); *C08F 4/65908* (2013.01); *C08F 4/65912* (2013.01); *C08F 4/65916* (2013.01); *C08F 4/65925* (2013.01); *C08F 4/65927* (2013.01); *C08F 210/16* (2013.01); *C08F 2410/01* (2013.01); *C08F 2410/03* (2013.01); *C08F 2420/04* (2013.01); *C08F 2420/06* (2013.01)

(58) Field of Classification Search
CPC ............. C08F 4/65904; C08F 4/65927; C08F 4/65923; C08F 4/65908; C08F 4/65912; C08F 210/16
See application file for complete search history.

(56) References Cited

U.S. PATENT DOCUMENTS

| 4,530,914 | A | 7/1985 | Ewen et al. |
| 6,153,551 | A | 11/2000 | Kissin et al. |
| 9,732,171 | B2* | 8/2017 | Sung ...................... C08F 4/6592 |
| 9,902,789 | B2* | 2/2018 | Hong ..................... C08F 210/16 |
| 9,975,969 | B2* | 5/2018 | Cho ........................ C08F 10/02 |
| 9,988,469 | B2* | 6/2018 | Song ......................... C08F 4/64 |
| 2006/0052238 | A1 | 3/2006 | Lee et al. |
| 2006/0235171 | A1 | 10/2006 | Lee et al. |
| 2006/0287449 | A1 | 12/2006 | Miyamoto et al. |
| 2012/0329966 | A1 | 12/2012 | Kwon et al. |
| 2013/0046068 | A1 | 2/2013 | Kwon et al. |
| 2013/0289227 | A1 | 10/2013 | Jensen et al. |
| 2014/0303332 | A1 | 10/2014 | Yang et al. |
| 2016/0222139 | A1 | 8/2016 | Cho et al. |
| 2016/0304637 | A1 | 10/2016 | Lee et al. |
| 2018/0037676 | A1 | 2/2018 | Song et al. |

FOREIGN PATENT DOCUMENTS

| EP | 1605000 A1 | 12/2005 |
| EP | 3246343 A1 | 11/2017 |
| JP | 07-091328 B2 | 10/1995 |
| JP | 2000-239310 A | 9/2000 |
| JP | 2007519781 A | 7/2007 |
| JP | 2016537500 A | 12/2016 |
| JP | 2016538373 A1 | 12/2016 |
| KR | 10-2001-0021779 A | 3/2001 |
| KR | 10-0579843 B1 | 5/2006 |
| KR | 10-0691576 B1 | 3/2007 |
| KR | 10-2011-0101386 A | 9/2011 |
| KR | 10-2013-0057813 A | 6/2013 |
| KR | 10-2014-0114310 A | 9/2014 |
| KR | 10-1474114 B1 | 12/2014 |
| KR | 10-1495423 B1 | 2/2015 |
| KR | 10-2015-0057974 A | 5/2015 |
| KR | 10-2015-0058035 B | 5/2015 |
| KR | 10-2015-0059125 A | 5/2015 |
| KR | 10-2015-0062145 A | 6/2015 |

(Continued)

OTHER PUBLICATIONS

Petasis et al., "Titanium-Mediated Carbonyl Olefinations. 1. Methylenations of Carbonyl Compounds with Dimethyltitanocene", J. Am. Chem. Soc. 1990, 112, 6392-6394.

(Continued)

*Primary Examiner* — Caixia Lu
(74) *Attorney, Agent, or Firm* — Dentons US LLP

(57) ABSTRACT

A method of preparing a supported metallocene catalyst capable of more effectively preparing a polyolefin which may be preferably used for blow molding, etc., because its molecular weight distribution is such that polymer elasticity is increased to improve swell, is provided.

13 Claims, 3 Drawing Sheets

(56) References Cited

FOREIGN PATENT DOCUMENTS

| KR | 10-1528603 B1 | 6/2015 |
|---|---|---|
| WO | 2012/097146 A1 | 7/2012 |
| WO | 2015076618 A1 | 5/2015 |
| WO | 2015080523 A1 | 6/2015 |

OTHER PUBLICATIONS

Petasis et al. "Ring-Opening Metathesis Polymerization of Norbornene with Titanium Alkylidenes Generated by Thermolysis of Dimethyltitanocene and Related Cyclopentadienyltitanium(1V) Derivatives", J. Am. Chem. SOC. 1993,115, 7208-7214.

Nicolau et al. "Olefin Metathesis in Cyclic Ether Formation. Direct Conversion of Olefinic Esters to Cyclic Enol Ethers with Tebbe-Type Reagents", J. Am. Chem. Soc. 1996, 118, 1565-1566.

\* cited by examiner

METHOD OF PREPARING SUPPORTED METALLOCENE CATALYST

CROSS-REFERENCE TO RELATED APPLICATION

This application is a National Stage Entry of International Application No. PCT/KR2016/006264, filed on Jun. 13, 2016, and claims the benefit of Korean Application No. 10-2015-0084483, filed on Jun. 15, 2015, and Korean Application No. 10-2016-0029835, filed on Mar. 11, 2016, all of which are hereby incorporated by reference in their entirety for all purposes as if fully set forth herein.

TECHNICAL FIELD

The present invention relates to a method of preparing a supported metallocene catalyst capable of more effectively preparing a polyolefin which may be preferably used for blow molding, etc., because its molecular weight distribution is such that polymer elasticity is increased to improve swell.

BACKGROUND OF THE INVENTION

In general, blow-molded articles are required to have excellent processability, mechanical properties, and stress cracking resistance. Therefore, there has been a demand for a technology for preparing a polyolefin which satisfies a high molecular weight, a broader multimodal molecular weight distribution, and a uniform comonomer distribution to be preferably used for blow-molding or the like.

Meanwhile, since metallocene catalysts including a Group 4 transition metal are used to easily control the molecular weight and molecular weight distribution of polyolefins, compared to the known Ziegler-Natta catalysts, and to control a comonomer distribution of polymers, they have been used in the preparation of polyolefins having improved mechanical properties and processability. However, there is a drawback that polyolefins prepared by using the metallocene catalysts show poor processability because of a narrow molecular weight distribution.

In general, polymers having a broad molecular weight distribution exhibit a great reduction in viscosity with an increasing shear rate, and thus exhibit excellent processability in the processing area. Polyolefins prepared by metallocene catalysts show high viscosity at a high shear rate due to a relatively narrow molecular weight distribution, etc., and thus there are drawbacks that a high load or pressure is applied during extrusion to reduce extrusion productivity, bubble stability is greatly reduced upon a blow-molding process, the blow-molded articles have non-uniform surfaces to have reduced transparency, etc.

In addition, a Tebbe reagent, which is a complex of titanocene and alkyl aluminum, has been used in ethylene polymerizations, and has functioned to increase a molecular weight. The main characteristic of the Tebbe reagent is known to be that the Tebbe reagent is activated by a base to form titanium alkylidene, leading to double bond-related reactions (olefination, metathesis, etc.). However, the role of the Tebbe reagent in ethylene polymerization where no Lewis base is added is not clearly known.

In 1990, the Petasis group succeeded in ring closing metathesis by simply heating the Tebbe reagent. It is believed that when the Tebbe reagent participates in polymerization, titanium alkylidene is formed by the polymerization temperature, resulting in polymerization using an alkylidene-specific reaction.

Therefore, there is a continuous demand for a technology capable of more effectively preparing a polyolefin which may be preferably used for blow molding, etc. while satisfying mechanical properties and processability at the same time, because its molecular weight distribution is such that polymer elasticity is increased to improve swell.

DETAILS OF THE INVENTION

Objects of the Invention

Accordingly, the present invention provides a method of preparing a supported metallocene catalyst capable of more effectively preparing a polyolefin which may be preferably used for blow molding, etc., because its molecular weight distribution is such that polymer elasticity is increased to improve swell.

Further, the present invention provides a polyolefin which is prepared in the presence of the supported metallocene catalyst prepared by the above preparation method, thereby satisfying mechanical properties and processability at the same time, and being preferably used for blow molding, etc.

Means for Achieving the Object

The present invention provides a method of preparing a supported metallocene catalyst, the method including: preparing a molecular weight modifier composition by mixing a cyclopentadienyl metal compound of the following Chemical Formula 1 and an organic aluminum compound of the following Chemical Formula 2 and stirring a resulting mixture at room temperature for 50 hours (h) to 108 hours (h); and supporting one or more metallocene compounds represented by any one of the following Chemical Formulae 3 to 6 and the molecular weight modifier composition on a support:

$$(R^1-Cp^1)(R^2-Cp^2)M^4X_2 \qquad \text{Chemical Formula 1}$$

in Chemical Formula 1, $Cp^1$ and $Cp^2$ are each independently a ligand including a cyclopentadienyl group, an indenyl group, or a fluorenyl group; $R^1$ and $R^2$ are substituents of $Cp^1$ and $Cp^2$, and are each independently hydrogen, an alkyl group having 1 to 20 carbon atoms, an alkenyl group having 1 to 20 carbon atoms, an alkylaryl group having 7 to 20 carbon atoms, an arylalkyl group having 7 to 20 carbon atoms, an aryl group having 6 to 20 carbon atoms, a heteroalkyl group having 1 to 20 carbon atoms, a heteroalkenyl group having 2 to 20 carbon atoms, a heteroalkylaryl group having 6 to 20 carbon atoms, a heteroarylalkyl group having 6 to 20 carbon atoms, or a heteroaryl group having 5 to 20 carbon atoms; $M^4$ is a Group 4 transition metal element; and X is a halogen, $$R^3R^4R^5Al \qquad \text{Chemical Formula 2}$$

in Chemical Formula 2, $R^3$, $R^4$, and $R^5$ are each independently an alkyl group having 4 to 20 carbon atoms or a halogen, and at least one of $R^3$, $R^4$, and $R^5$ is an alkyl group having 4 to 20 carbon atoms, $$(Cp^5R^a)_n(Cp^6R^b)M^1Z^1_{3-n} \qquad \text{Chemical Formula 3}$$

in Chemical Formula 3, $M^1$ is a Group 4 transition metal; $Cp^5$ and $Cp^6$ are the same as or different from each other, and are each independently any one selected from the group consisting of cyclopentadienyl, indenyl, 4,5,6,7-tetrahydro- 1-indenyl, and fluorenyl radicals, and these may be substituted with a hydrocarbon having 1 to 20 carbon atoms;

$R^a$ and $R^b$ are the same as or different from each other, and are each independently hydrogen, a C1 to C20 alkyl, a C1 to C10 alkoxy, a C2 to C20 alkoxyalkyl, a C6 to C20 aryl, a C6 to C10 aryloxy, a C2 to C20 alkenyl, a C7 to C40 alkylaryl, a C7 to C40 arylalkyl, a C8 to C40 arylalkenyl, or a C2 to C10 alkynyl;

$Z^1$ is a halogen atom, a C1 to C20 alkyl, a C2 to C10 alkenyl, a C7 to C40 alkylaryl, a C7 to C40 arylalkyl, a C6 to C20 aryl, a substituted or unsubstituted C1 to C20 alkylidene, a substituted or unsubstituted amino group, a C2 to C20 alkylalkoxy, or a C7 to C40 arylalkoxy; and n is 1 or 0,

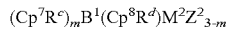  Chemical Formula 4 in Chemical Formula 4, $M^2$ is a Group 4 transition metal;

$Cp^7$ and $Cp^8$ are the same as or different from each other, and are each independently any one selected from the group consisting of cyclopentadienyl, indenyl, 4,5,6,7-tetrahydro-1-indenyl, and fluorenyl radicals, and these are substituted with a hydrocarbon having 1 to 20 carbon atoms;

$R^c$ and $R^d$ are the same as or different from each other, and are each independently hydrogen, a C1 to C20 alkyl, a C1 to C10 alkoxy, a C2 to C20 alkoxyalkyl, a C6 to C20 aryl, a C6 to C10 aryloxy, a C2 to C20 alkenyl, a C7 to C40 alkylaryl, a C7 to C40 arylalkyl, a C8 to C40 arylalkenyl, or a C2 to C10 alkynyl;

$Z^2$ is a halogen atom, a C1 to C20 alkyl, a C2 to C10 alkenyl, a C7 to C40 alkylaryl, a C7 to C40 arylalkyl, a C6 to C20 aryl, a substituted or unsubstituted C1 to C20 alkylidene, a substituted or unsubstituted amino group, a C2 to C20 alkylalkoxy, or a C7 to C40 arylalkoxy;

$B^1$ is any one or more of carbon, germanium, silicon, phosphorus, or nitrogen atom-containing radicals, which crosslink a $Cp^3R^c$ ring and a $Cp^4R^d$ ring or crosslink one $Cp^4R^d$ ring to $M^2$, or a combination thereof; and m is 1 or 0,

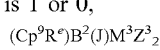  Chemical Formula 5 in Chemical Formula 5, $M^3$ is a Group 4 transition metal;

$Cp^9$ is any one selected from the group consisting of cyclopentadienyl, indenyl, 4,5,6,7-tetrahydro-1-indenyl, and fluorenyl radicals, and these are substituted with a hydrocarbon having 1 to 20 carbon atoms;

$R^e$ is hydrogen, a C1 to C20 alkyl, a C1 to C10 alkoxy, a C2 to C20 alkoxyalkyl, a C6 to C20 aryl, a C6 to C10 aryloxy, a C2 to C20 alkenyl, a C7 to C40 alkylaryl, a C7 to C40 arylalkyl, a C8 to C40 arylalkenyl, or a C2 to C10 alkynyl;

$Z^3$ is a halogen atom, a C1 to C20 alkyl, a C2 to C10 alkenyl, a C7 to C40 alkylaryl, a C7 to C40 arylalkyl, a C6 to C20 aryl, a substituted or unsubstituted C1 to C20 alkylidene, a substituted or unsubstituted amino group, a C2 to C20 alkylalkoxy, or a C7 to C40 arylalkoxy;

$B^2$ is any one or more of carbon, germanium, silicon, phosphorus, or nitrogen atom-containing radicals, which crosslink a $Cp^5R^e$ ring to J, or a combination thereof; and J is any one selected from the group consisting of $NR^f$, O, $PR^f$ and S; and $R^f$ is a C1 to C20 alkyl, aryl, substituted alkyl, or substituted aryl,

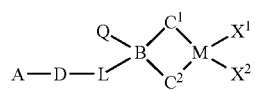  Chemical Formula 6 in Chemical Formula 6, A is hydrogen, a halogen, a C1 to C20 alkyl group, a C2 to C20 alkenyl group, a C6 to C20 aryl group, a C7 to C20 alkylaryl group, a C7 to C20 arylalkyl group, a C1 to C20 alkoxy group, a C2 to C20 alkoxyalkyl group, a C3 to C20 heterocycloalkyl group, or a C5 to C20 heteroaryl group;

D is —O—, —S—, —N(R)—, or —Si(R)(R')—, in which R and R' are the same as or different from each other, and are each independently hydrogen, a halogen, a C1 to C20 alkyl group, a C2 to C20 alkenyl group, or a C6 to C20 aryl group;

L is a C1 to C10 straight or branched alkylene group;

B is carbon, silicon, or germanium;

Q is hydrogen, a halogen, a C1 to C20 alkyl group, a C2 to C20 alkenyl group, a C6 to C20 aryl group, a C7 to C20 alkylaryl group, or a C7 to C20 arylalkyl group;

M is a Group 4 transition metal;

$X^1$ and $X^2$ are the same as or different from each other, and are each independently a halogen, a C1 to C20 alkyl group, a C2 to C20 alkenyl group, a C6 to C20 aryl group, a nitro group, an amido group, a C1 to C20 alkylsilyl group, a C1 to C20 alkoxy group, or a C1 to C20 sulfonate group; and $C^1$ and $C^2$ are the same as or different from each other, and are each independently represented by any one of the following Chemical Formula 7a, Chemical Formula 7b, and Chemical Formula 7c, excluding that both $C^1$ and $C^2$ are Chemical Formula 7c,

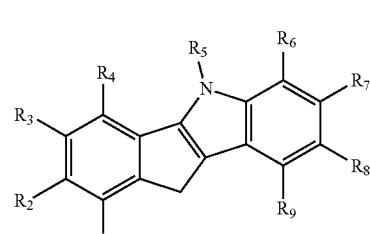

Chemical Formula 7a

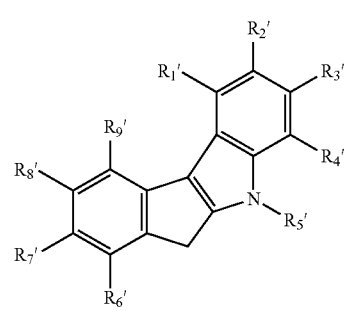

Chemical Formula 7b

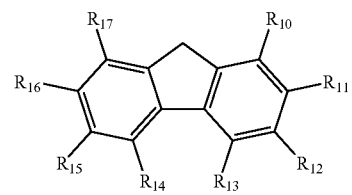

Chemical Formula 7c in Chemical Formulae 7a, 7b, and 7c, $R_1$ to $R_{17}$ and $R_1'$ to $R_9'$ are the same as or different from each other, and are each independently hydrogen, a halogen, a C1 to C20 alkyl group, a C2 to C20 alkenyl group, a C1 to C20 alkylsilyl group, a C1 to C20 silylalkyl group, a C1 to C20 alkoxysilyl group, a C1 to C20 alkoxy group, a C6 to C20 aryl group, a C7 to C20 alkylaryl group, or a C7 to C20 arylalkyl group, and two or more neighboring groups of $R_{10}$ to $R_{17}$ are connected to each other to form a substituted or unsubstituted aliphatic or aromatic ring.

Further, the present invention provides a method of preparing a polyolefin, the method including polymerizing olefinic monomers in the presence of the supported metallocene catalyst.

Furthermore, the present invention provides a polyolefin prepared according to the above preparation method.

Hereinafter, a method of preparing a supported metallocene catalyst according to embodiments of the present invention, a supported metallocene catalyst prepared therefrom, a method of preparing a polyolefin using the same, and a polyolefin prepared therefrom will be described.

According to an embodiment of the present invention, a supported metallocene catalyst is prepared by supporting a metallocene compound and a particular molecular weight modifier composition on a support. A method of preparing the supported metallocene catalyst includes: preparing a molecular weight modifier composition by mixing a cyclopentadienyl metal compound of the following Chemical Formula 1 and an organic aluminum compound of the following Chemical Formula 2 and stirring a resulting mixture at room temperature for 50 hours (h) to 108 hours (h); and supporting one or more metallocene compounds represented by any one of the following Chemical Formulae 3 to 6 and the molecular weight modifier composition on a support:

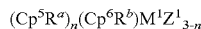  Chemical Formula 3 in Chemical Formula 3, $M^1$ is a Group 4 transition metal;

$Cp^5$ and $Cp^6$ are the same as or different from each other, and are each independently any one selected from the group consisting of cyclopentadienyl, indenyl, 4,5,6,7-tetrahydro-1-indenyl, and fluorenyl radicals, and these may be substituted with a hydrocarbon having 1 to 20 carbon atoms;

$R^a$ and $R^b$ are the same as or different from each other, and are each independently hydrogen, a C1 to C20 alkyl, a C1 to C10 alkoxy, a C2 to C20 alkoxyalkyl, a C6 to C20 aryl, a C6 to C10 aryloxy, a C2 to C20 alkenyl, a C7 to C40 alkylaryl, a C7 to C40 arylalkyl, a C8 to C40 arylalkenyl, or a C2 to C10 alkynyl;

$Z^1$ is a halogen atom, a C1 to C20 alkyl, a C2 to C10 alkenyl, a C7 to C40 alkylaryl, a C7 to C40 arylalkyl, a C6 to C20 aryl, a substituted or unsubstituted C1 to C20 alkylidene, a substituted or unsubstituted amino group, a C2 to C20 alkylalkoxy, or a C7 to C40 arylalkoxy; and n is 1 or 0,

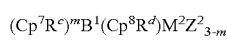  Chemical Formula 4 in Chemical Formula 4, $M^2$ is a Group 4 transition metal;

$Cp^7$ and $Cp^8$ are the same as or different from each other, and are each independently any one selected from the group consisting of cyclopentadienyl, indenyl, 4,5,6,7-tetrahydro-1-indenyl, and fluorenyl radicals, and these are substituted with a hydrocarbon having 1 to 20 carbon atoms;

$R^c$ and $R^d$ are the same as or different from each other, and are each independently hydrogen, a C1 to C20 alkyl, a C1 to C10 alkoxy, a C2 to C20 alkoxyalkyl, a C6 to C20 aryl, a C6 to C10 aryloxy, a C2 to C20 alkenyl, a C7 to C40 alkylaryl, a C7 to C40 arylalkyl, a C8 to C40 arylalkenyl, or a C2 to C10 alkynyl;

$Z^2$ is a halogen atom, a C1 to C20 alkyl, a C2 to C10 alkenyl, a C7 to C40 alkylaryl, a C7 to C40 arylalkyl, a C6 to C20 aryl, a substituted or unsubstituted C1 to C20 alkylidene, a substituted or unsubstituted amino group, a C2 to C20 alkylalkoxy, or a C7 to C40 arylalkoxy;

$B^1$ is any one or more of carbon, germanium, silicon, phosphorus, or nitrogen atom-containing radicals, which crosslink a $Cp^3R^c$ ring and a $Cp^4R^d$ ring or crosslink one $Cp^4R^d$ ring to $M^2$, or a combination thereof; and m is 1 or 0,

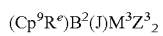  Chemical Formula 5 in Chemical Formula 5, $M^3$ is a Group 4 transition metal;

$Cp^9$ is any one selected from the group consisting of cyclopentadienyl, indenyl, 4,5,6,7-tetrahydro-1-indenyl, and fluorenyl radicals, and these are substituted with a hydrocarbon having 1 to 20 carbon atoms;

$R^e$ is hydrogen, a C1 to C20 alkyl, a C1 to C10 alkoxy, a C2 to C20 alkoxyalkyl, a C6 to C20 aryl, a C6 to C10 aryloxy, a C2 to C20 alkenyl, a C7 to C40 alkylaryl, a C7 to C40 arylalkyl, a C8 to C40 arylalkenyl, or a C2 to C10 alkynyl;

$Z^3$ is a halogen atom, a C1 to C20 alkyl, a C2 to C10 alkenyl, a C7 to C40 alkylaryl, a C7 to C40 arylalkyl, a C6 to C20 aryl, a substituted or unsubstituted C1 to C20 alkylidene, a substituted or unsubstituted amino group, a C2 to C20 alkylalkoxy, or a C7 to C40 arylalkoxy;

$B^2$ is any one or more of carbon, germanium, silicon, phosphorus, or nitrogen atom-containing radicals, which crosslink a $Cp^5R^e$ ring to J, or a combination thereof; and J is any one selected from the group consisting of $NR^f$, O, $PR^f$, and S; and $R^f$ is a C1 to C20 alkyl, aryl, substituted alkyl, or substituted aryl,

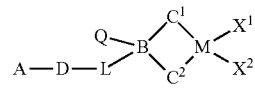  Chemical Formula 6 in Chemical Formula 6, A is hydrogen, a halogen, a C1 to C20 alkyl group, a C2 to C20 alkenyl group, a C6 to C20 aryl group, a C7 to C20 alkylaryl group, a C7 to C20 arylalkyl group, a C1 to C20 alkoxy group, a C2 to C20 alkoxyalkyl group, a C3 to C20 heterocycloalkyl group, or a C5 to C20 heteroaryl group;

D is —O—, —S—, —N(R)—, or —Si(R)(R')—, in which R and R' are the same as or different from each other, and are each independently hydrogen, a halogen, a C1 to C20 alkyl group, a C2 to C20 alkenyl group, or a C6 to C20 aryl group;

L is a C1 to C10 straight or branched alkylene group;

B is carbon, silicon, or germanium;

Q is hydrogen, a halogen, a C1 to C20 alkyl group, a C2 to C20 alkenyl group, a C6 to C20 aryl group, a C7 to C20 alkylaryl group, or a C7 to C20 arylalkyl group;

M is a Group 4 transition metal;

$X^1$ and $X^2$ are the same as or different from each other, and are each independently a halogen, a C1 to C20 alkyl group, a C2 to C20 alkenyl group, a C6 to C20 aryl group, a nitro group, an amido group, a C1 to C20 alkylsilyl group, a C1 to C20 alkoxy group, or a C1 to C20 sulfonate group; and $C^1$ and $C^2$ are the same as or different from each other, and are each independently represented by any one of the following Chemical Formula 7a, Chemical Formula 7b, and Chemical Formula 7c, excluding that both $C^1$ and $C^2$ are Chemical Formula 7c, Chemical Formula 7a

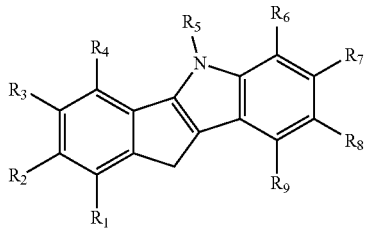

Chemical Formula 7b

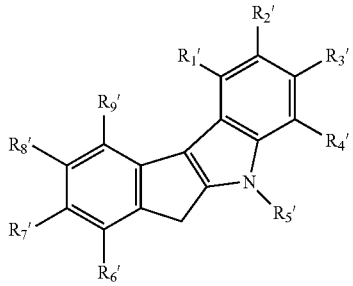

Chemical Formula 7c

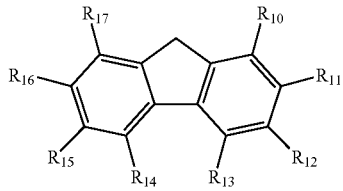

in Chemical Formulae 7a, 7b, and 7c, $R_1$ to $R_{17}$ and $R_1'$ to $R_9'$ are the same as or different from each other, and are each independently hydrogen, a halogen, a C1 to C20 alkyl group, a C2 to C20 alkenyl group, a C1 to C20 alkylsilyl group, a C1 to C20 silylalkyl group, a C1 to C20 alkoxysilyl group, a C1 to C20 alkoxy group, a C6 to C20 aryl group, a C7 to C20 alkylaryl group, or a C7 to C20 arylalkyl group, and two or more neighboring groups of $R_{10}$ to $R_{17}$ are connected to each other to form a substituted or unsubstituted aliphatic or aromatic ring, $(R^1\text{-}Cp^1)(R^2\text{-}Cp^2)M^4X_2$  Chemical Formula 1 in Chemical Formula 1, $Cp^1$ and $Cp^2$ are each independently a ligand including a cyclopentadienyl group, an indenyl group, or a fluorenyl group; $R^1$ and $R^2$ are substituents of $Cp^1$ and $Cp^2$, and are each independently hydrogen, an alkyl having 1 to 20 carbon atoms, an alkenyl having 1 to 20 carbon atoms, an alkylaryl having 7 to 20 carbon atoms, an arylalkyl having 7 to 20 carbon atoms, an aryl having 6 to 20 carbon atoms, a heteroalkyl having 1 to 20 carbon atoms, a heteroalkenyl having 2 to 20 carbon atoms, a heteroalkylaryl having 6 to 20 carbon atoms, a heteroarylalkyl having 6 to 20 carbon atoms, or a heteroaryl having 5 to 20 carbon atoms; $M^4$ is a Group 4 transition metal element; and X is a halogen. In particular, $R^1$ and $R^2$ may each independently be selected from the group consisting of hydrogen, methyl, ethyl, butyl, and t-butoxy hexyl. Further, $M^4$ may be a Group 4 transition metal element, and is preferably selected from the group consisting of titanium, zirconium, and hafnium. In addition, X may be a halogen, and is preferably selected from the group consisting of F, Cl, Br, and I.

$R^3R^4R^5Al$  Chemical Formula 2

Herein, in Chemical Formula 2, $R^3$, $R^4$, and $R^5$ are each independently an alkyl group having 4 to 20 carbon atoms or a halogen, and at least one of $R^3$, $R^4$, and $R^5$ is an alkyl group having 4 to 20 carbon atoms. In particular, $R^3$, $R^4$, and $R^5$ may each independently be an isobutyl group.

Experimental results of the present inventors showed that when a metallocene catalyst including a mixture of a particular molecular weight modifier composition and a catalyst precursor is used, it is possible to prepare a polyolefin having a higher molecular weight and a broader molecular weight distribution with improved activity. A mechanism of action of the molecular weight modifier has not been clearly revealed. However, it is assumed that when the particular molecular weight modifier is mixed with the catalyst precursor, a metal alkylidene formed from an early-transition metal belonging to Groups 3 to 7 of the Periodic Table has a difference in partial charge quantity between the metal and the alkyl group, and therefore, alkylidene having a partial negative charge binds to the metallocene of the early-transition metal which is more Lewis-acidic than aluminum alkyl, thereby having a bridge-shaped intermediate, and as a result, a molecular weight is increased, leading to preparation of a polyolefin having a higher molecular weight and a broader molecular weight distribution.

According to a specific embodiment of the present invention, a supported metallocene catalyst may be prepared by reacting the above-described metallocene compound with a particular molecular weight modifier composition and then supporting a reaction product on a support, as in the following Reaction Scheme 1.

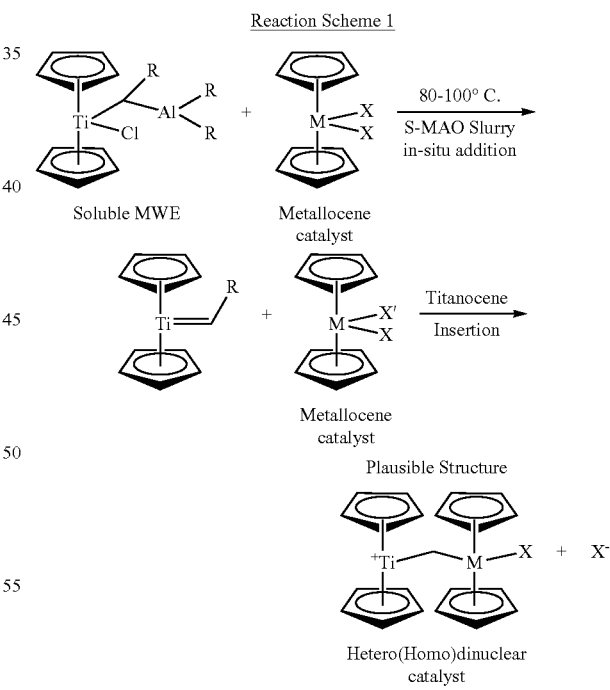

Reaction Scheme 1

In the present invention, particularly, the concept of the molecular weight control action by change of hydrogen reactivity of the existing Tebbe-type reagent is further expanded to provide a technology for controlling the molecular weight by inducing a direct reaction between the precursor and titanocene and controlling hydrogen reactivity using a smaller amount of titanocene. When an unnecessary molecular weight modifier is used, unreacted organic aluminum remaining during a process may exist, and this compound may cause process instability in a subsequent process. That is, the present invention is characterized by enabling efficient molecular weight control by using a minimum amount of the molecular weight modifier.

In the preparation method of an embodiment, the molecular weight modifier composition may be produced by mixing the cyclopentadienyl metal compound of Chemical Formula 1 and the organic aluminum compound of Chemical Formula 2 at 0.1 to 1.0 equivalent weight (eq.), preferably 0.1 to 0.5 equivalent weight, and then stirring a mixture at room temperature, for example, at 22.5 to 25° C. for 50 h to 108 h, preferably for 62 h to 90 h. The molecular weight modifier composition may include a mixture of the cyclopentadienyl metal compound of Chemical Formula 1 and the organic aluminum compound of Chemical Formula 2, or a reaction product thereof, for example, an organic metal complex resulting from a reaction of the compounds of Chemical Formula 1 and Chemical Formula 2.

Further, the molecular weight modifier including particular substituents in the cyclopentadienyl group of Chemical Formula 1 and the organic functional group of Chemical Formula 2 exhibits remarkably improved solubility, compared to the existing molecular weight modifiers, and thus it has excellent homogeneity with respect to the catalyst precursor. Therefore, the catalyst composition may be uniformly formed to exhibit excellent polymerization performance.

According to an embodiment, the supported metallocene catalyst of the present invention may be used to more effectively prepare a polyolefin which may exhibit superior mechanical properties and processability and may be preferably used for blow molding, etc., because its molecular weight distribution is such that the molecular weight and polymer elasticity are further increased to improve swell.

The molecular weight modifier produced by reaction of the cyclopentadienyl metal compound of Chemical Formula 1 and the organic aluminum compound of Chemical Formula 2 may be represented by the following Chemical Formula 8, Chemical Formula 9, Chemical Formula 10, or Chemical Formula 11.

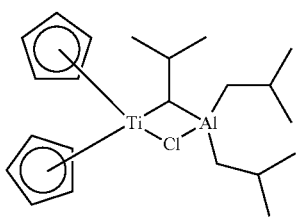

Chemical Formula 8

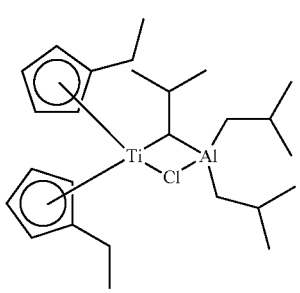

Chemical Formula 9

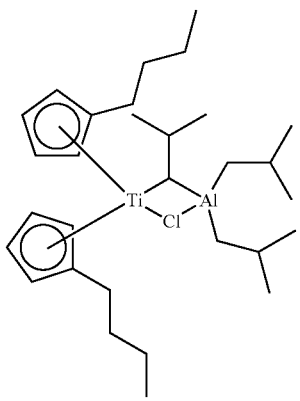

Chemical Formula 10

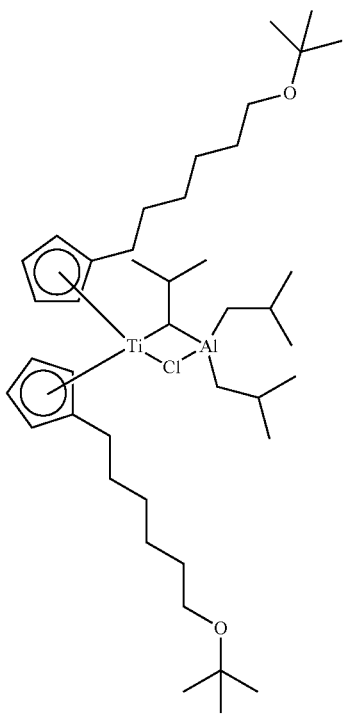

Chemical Formula 11

Meanwhile, when titanocene is used alone in a known manner, polymerization rarely occurs, and a Tebbe-type reagent does not participate in polymerization. As organic lithium or organic magnesium acts as a strong base, they have a mechanism which is not related with titanocene carbene. The present invention focused on chemical reactions arising from carbene of titanium carbene which is generated by thermal decomposition of organic aluminum-bound titanocene. The present invention is advantageous in that a maximum molecular weight control effect may be obtained by using a minimal amount of titanocene by more positively causing a chemical reaction in a metallocene precursor which plays the most important role in polymer formation.

In the preparation method of an embodiment, the molecular weight modifier composition may include the compounds of Chemical Formulae 1 and 2 in the form of an unreacted mixture thereof, or a reaction product of the compounds of Chemical Formulae 1 and 2, for example, in the form of an organic metal complex, in which metal atoms of these compounds are connected to each other via X and/or any one of $R^1$, $R^2$, and $R^3$. In this regard, the molecular weight modifier may further include unreacted compound(s) of Chemical Formula 1 and/or Chemical Formula 2, together with the organic metal complex.

As described above, the molecular weight modifier aids the activity of the metallocene catalyst to allow polymerization with high activity in the presence of a
relatively small amount of the metallocene catalyst and to prepare a polyolefin having a molecular weight distribution whereby the molecular weight and polymer elasticity are further increased to improve swell.

In the molecular weight modifier composition, specific examples of the cyclopentadienyl-based metal compound of Chemical Formula 3 may include bis(cyclopentadienyl) titanium dichloride, bis(cyclopentadienyl)zirconium dichloride, bis(cyclopentadienyl)hafnium dichloride, bis(indenyl) titanium dichloride, bis(fluorenyl)titanium dichloride, bis(2-ethylcyclopenta-2,4-dien-1-yl)titanium dichloride, bis(2-butylcyclopenta-2,4-dien-1-yl)titanium dichloride, bis(2-(6-t-butoxy-hexyl)cyclopenta-2,3-dien-1-yl)titanium dichloride, bis(2-ethylcyclopenta-2,4-dien-1-yl)zirconium dichloride, bis(2-ethylcyclopenta-2,4-dien-1-yl)hafnium dichloride, etc. Specific examples of the organic aluminum compound of Chemical Formula 4 may include triisobutyl aluminum, trihexylaluminum, trioctyl aluminum, diisobutylaluminum chloride, dihexylaluminum chloride, isobutylaluminum dichloride, etc.

The compound of Chemical Formula 1 and the compound of Chemical Formula 2 are preferably used at a molar ratio of a metal element (M) included in Chemical Formula 3 to aluminum (Al) included in Chemical Formula 4 of about 1:0.1 to about 1:100, or about 1:0.5 to about 1:10.

The molecular weight modifier may be used in an amount of about 0.1 to 10 parts by weight, or about 0.1 to 1 parts by weight, based on a total of 100 parts by weight of the catalyst precursor. The molecular weight modifier may be used in an amount of about 1 to 85 mol %, preferably about 3 to 70 mol %, more preferably about 5 to 55 mol %, or 10 to 50 mol %, based on the total weight of the catalyst precursor. When the molecular weight modifier is used in an amount within the above range, the action and effect due to addition of the molecular weight modifier are optimized to obtain a polyolefin having a low polymer melt index, a broad molecular weight distribution, a high molecular weight, and more improved stress cracking resistance, considering density or polymer melt index. In particular, when organic aluminum, etc. is excessively present in a reactor, it reacts with the metallocene catalyst, like a general alkyl aluminum, thereby causing deactivation of the metallocene catalyst and reducing the catalytic activity thereof. Therefore, the present invention is advantageous in that the molecular weight modifier is reacted in a catalytic amount relative to the precursor with maximum efficiency, and thus the activity of the metallocene precursor itself is not inhibited. Further, although the molecular weight modifier is used in a small amount corresponding to the catalytic amount of the metallocene precursor which is supported during preparation of the supported metallocene catalyst, a molecular weight of the single or hybrid supported catalyst may be effectively controlled. The prior technologies are characterized by simply increasing the molecular weight, whereas the present invention is advantageous in that a polymer structure may be finely controlled according to an amount of the molecular weight modifier, while maintaining polymerization conditions where no activity reduction occurs. Further, there is no concern about non-uniformity of supporting due to instability of the interaction of the cocatalyst, e.g., MAO, etc. with the precursor during preparation of the supported catalyst, and therefore the present invention may provide a supported catalyst with excellent catalytic stability.

Meanwhile, in the preparation method of an embodiment, the supported metallocene catalyst is used in the form of a supported catalyst, in which the metallocene compound and the molecular weight modifier composition are supported on a support. Further, the metallocene catalyst may be a metallocene catalyst including a hybrid of two or more different metallocene compounds or only a single metallocene compound.

The metallocene compound represented by Chemical Formula 3 may be, for example, a compound represented by any one of the following structural formulae, but is not limited thereto.

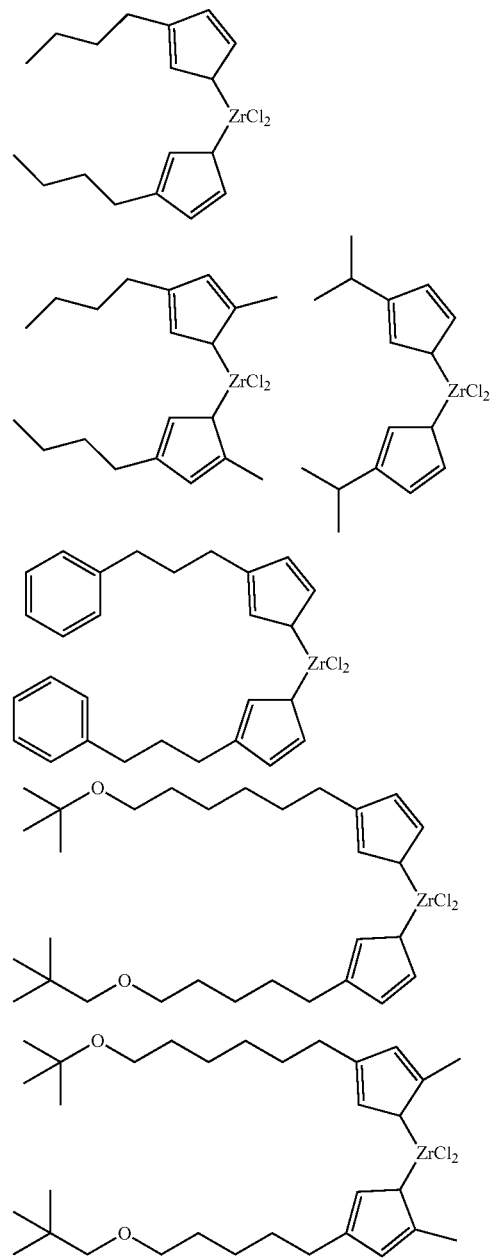

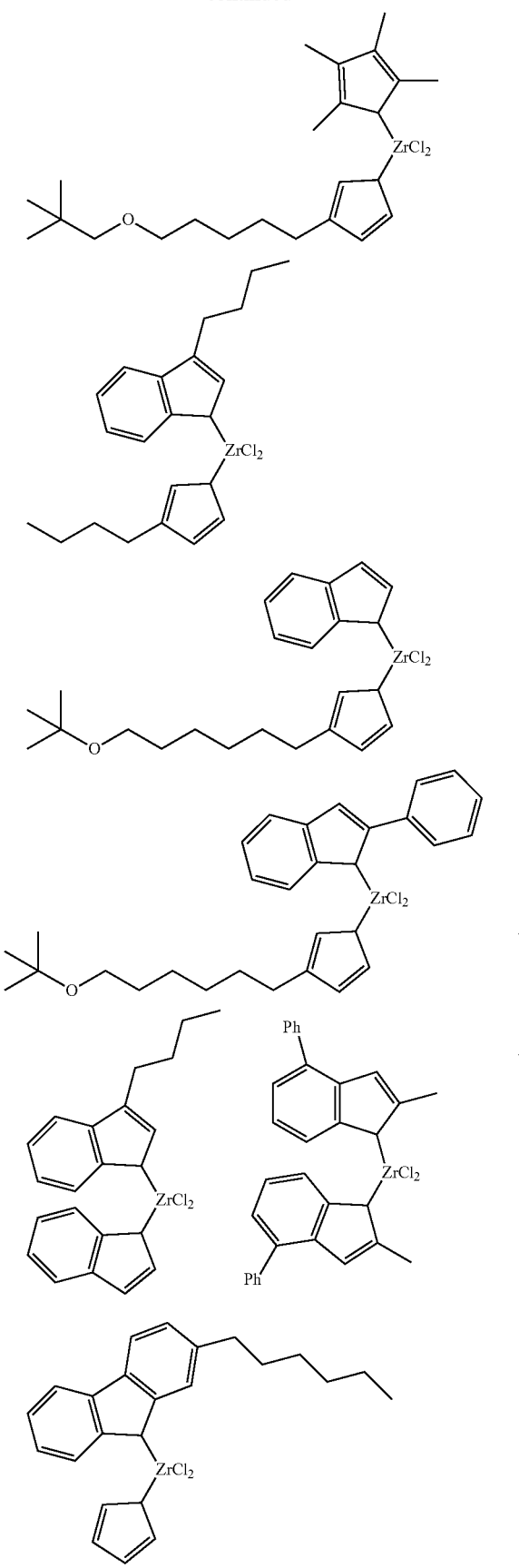
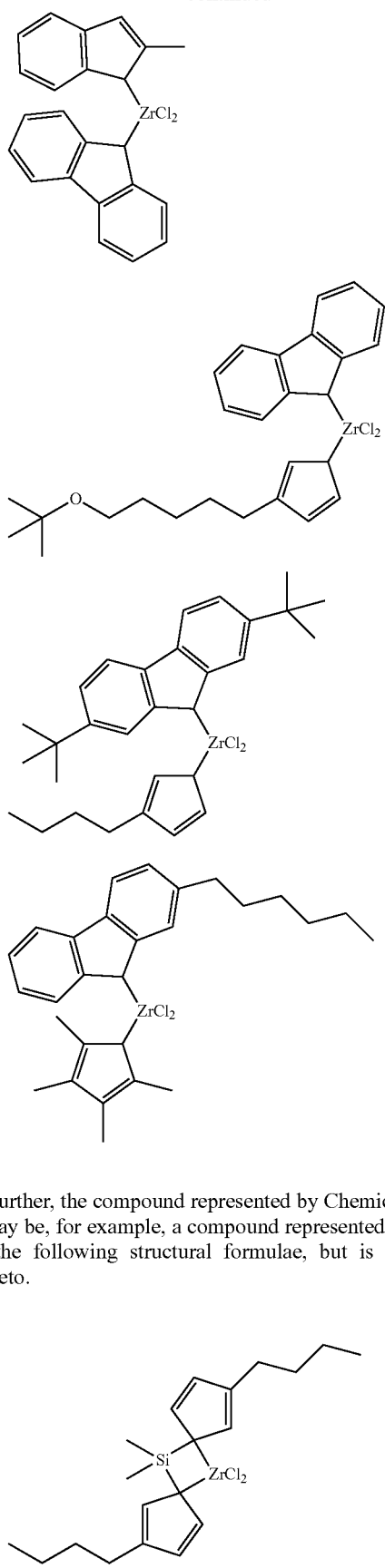
Further, the compound represented by Chemical Formula 4 may be, for example, a compound represented by any one of the following structural formulae, but is not limited thereto.

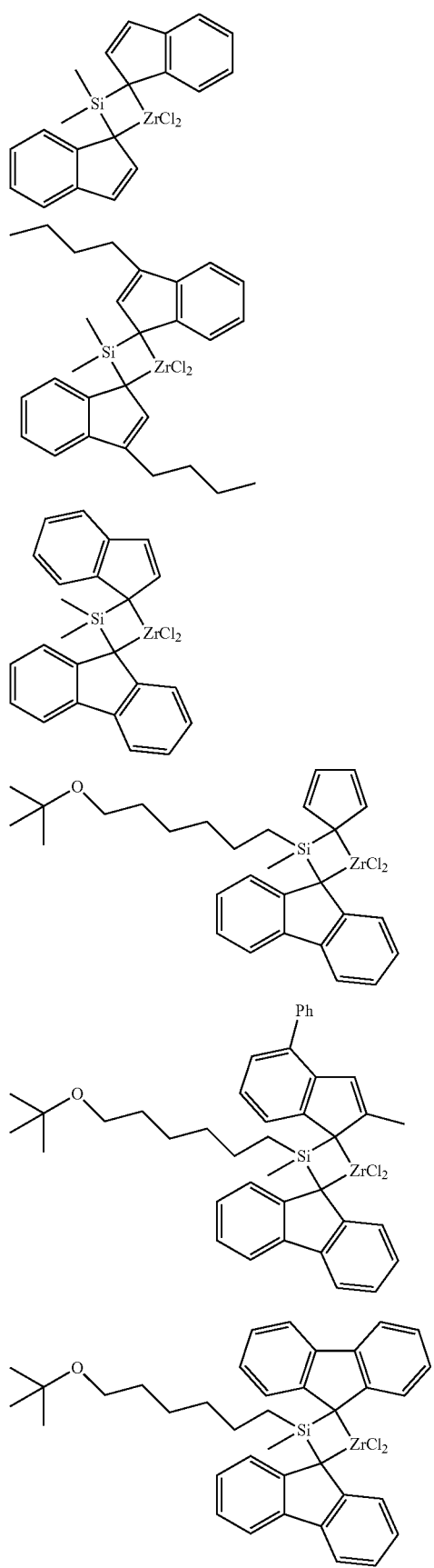
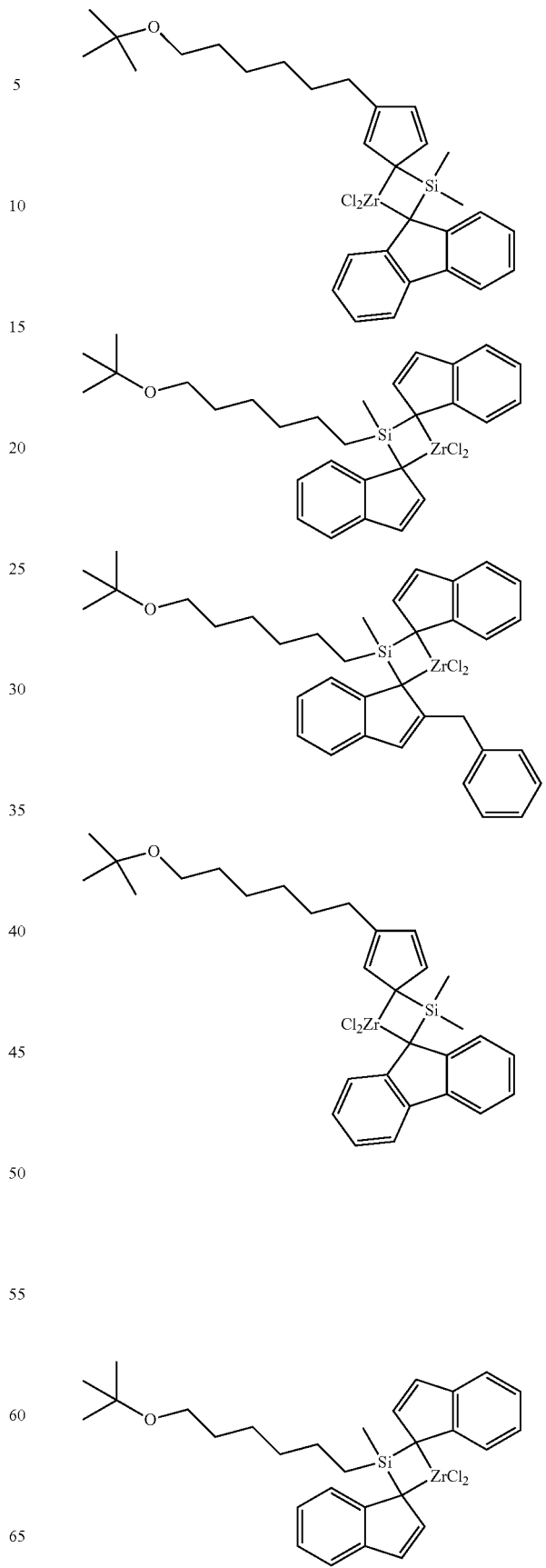

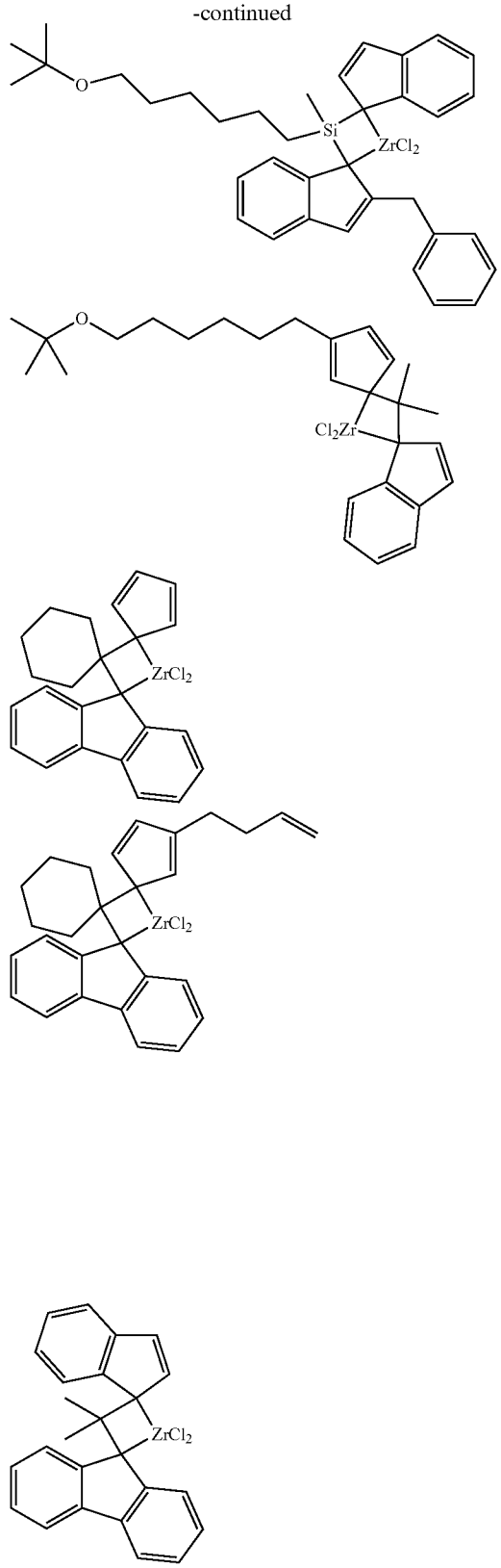
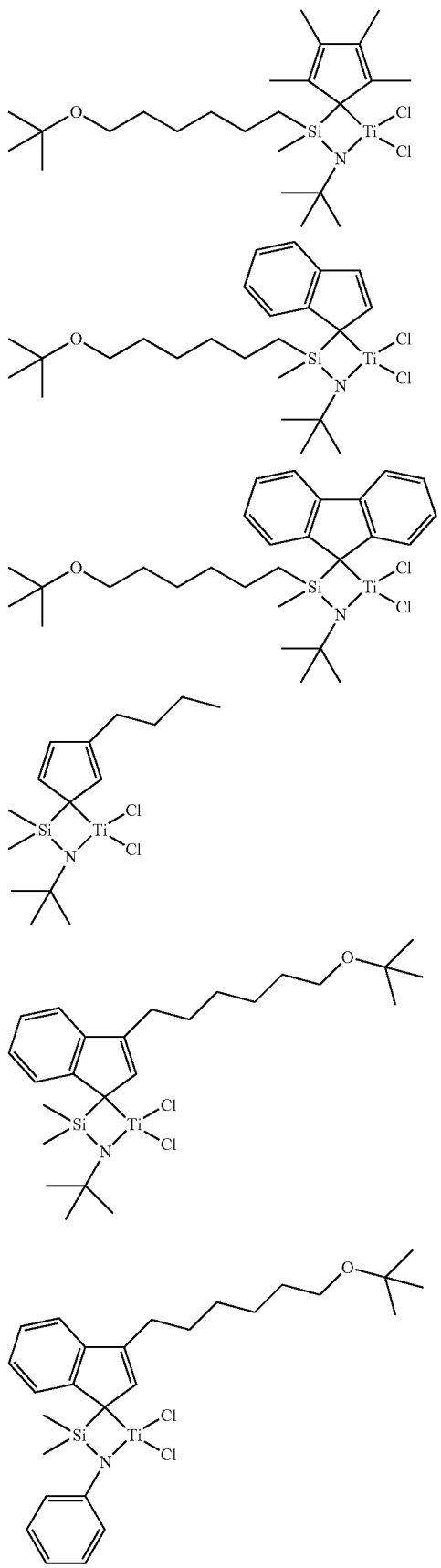
Further, the compound represented by Chemical Formula 5 may be, for example, a compound represented by any one of the following structural formulae, but is not limited thereto.

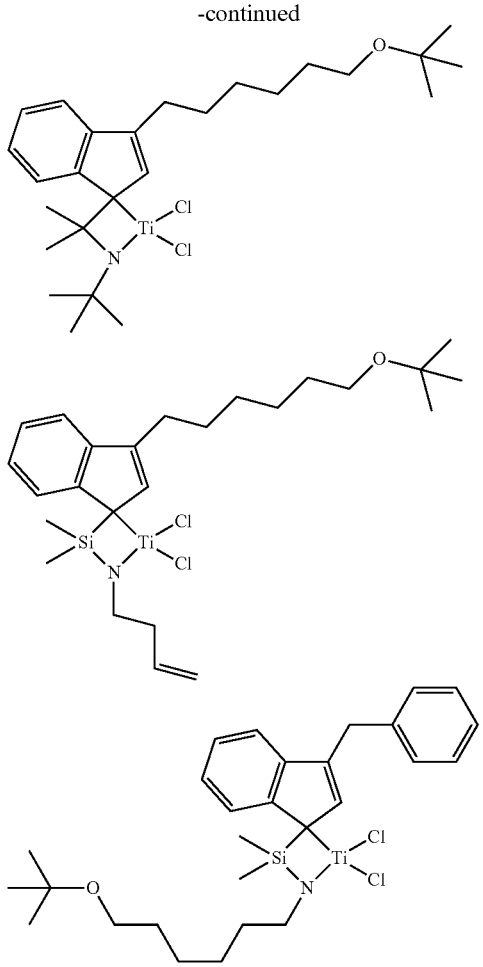

In Chemical Formula 6, the Group 4 transition metal (M) may be exemplified by titanium, zirconium, hafnium, etc., but is not limited thereto.

In the metallocene compound of Chemical Formula 6, $R_1$ to $R_{17}$ and $R_1'$ to $R_9'$ of Chemical Formulae 7a, 7b, and 7c are each independently hydrogen, a methyl group, an ethyl group, a propyl group, an isopropyl group, an n-butyl group, a tert-butyl group, a pentyl group, a hexyl group, a heptyl group, an octyl group, a phenyl group, a halogen group, a trimethylsilyl group, a triethylsilyl group, a tripropylsilyl group, a tributylsilyl group, a triisopropylsilyl group, a trimethylsilylmethyl group, a methoxy group, or an ethoxy group, but are not limited thereto.

In the metallocene compound of Chemical Formula 6, L is more preferably a C4 to C8 straight or branched alkylene group, but is not limited thereto. Further, the alkylene group may be substituted or unsubstituted with a C1 to C20 alkyl group, a C2 to C20 alkenyl group, or a C6 to C20 aryl group.

In the metallocene compound of Chemical Formula 6, A is preferably hydrogen, a methyl group, an ethyl group, a propyl group, an isopropyl group, an n-butyl group, a tert-butyl group, a methoxymethyl group, a tert-butoxymethyl group, a 1-ethoxyethyl group, a 1-methyl-1-methoxyethyl group, a tetrahydropyranyl group, or a tetrahydrofuranyl group, but is not limited thereto. Further, B is preferably silicon, but is not limited thereto.

The metallocene compound of Chemical Formula 6 may form a structure in which an indeno indole derivative and/or a fluorene derivative are/is crosslinked by a bridge, and it has an unshared electron pair which may function as a Lewis base in a ligand structure. Therefore, when the metallocene compound is supported on the surface having a Lewis acid property of a support, it shows high polymerization activity even when supported. Further, since the metallocene compound includes the electron-rich indeno indole group and/or fluorene group, it has low hydrogen reactivity due to proper steric hindrance and electronic effect of the ligand, and also maintains high activity even in the presence of hydrogen. Further, the nitrogen atom of the indeno indole derivative stabilizes beta-hydrogen of a growing polymer chain by a hydrogen bond to inhibit beta-hydrogen elimination, and therefore it is possible to polymerize an olefin polymer having a very high molecular weight.

According to an embodiment of the present invention, a specific example of the structure represented by Chemical Formula 7a may be a structure represented by any one of the following structural formulae, but is not limited thereto.

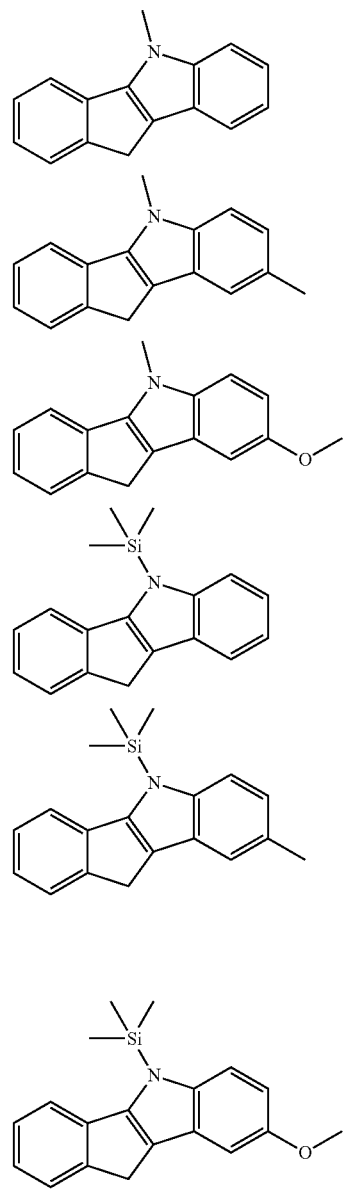

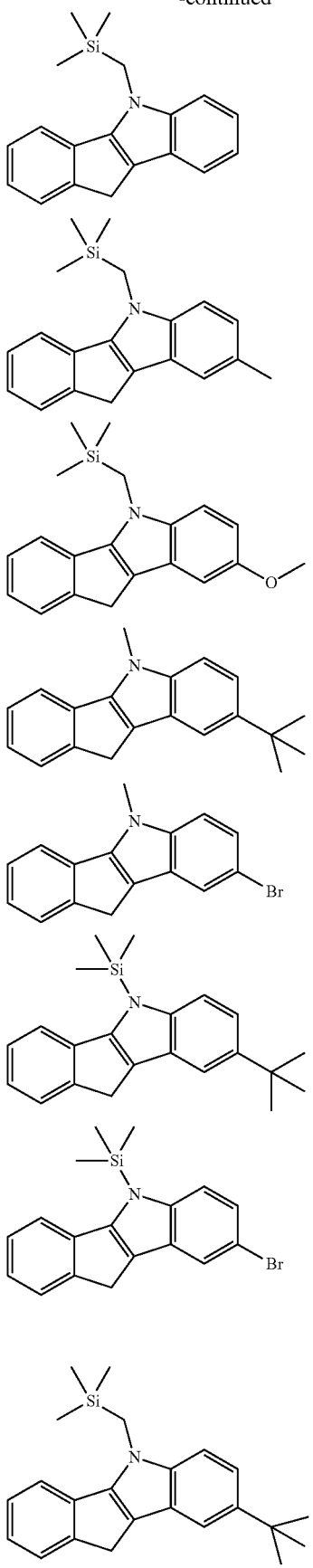
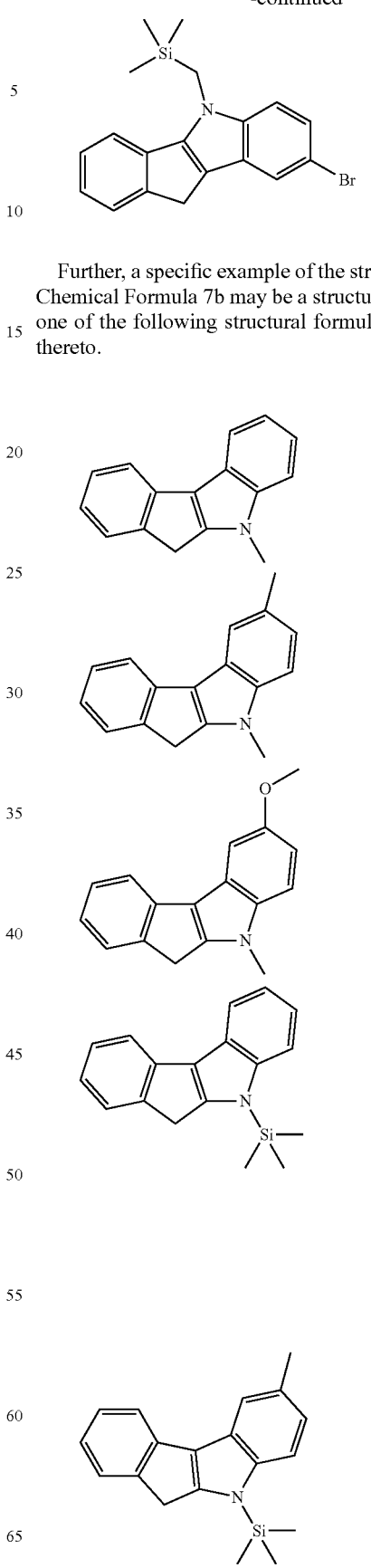
Further, a specific example of the structure represented by Chemical Formula 7b may be a structure represented by any one of the following structural formulae, but is not limited thereto.

-continued
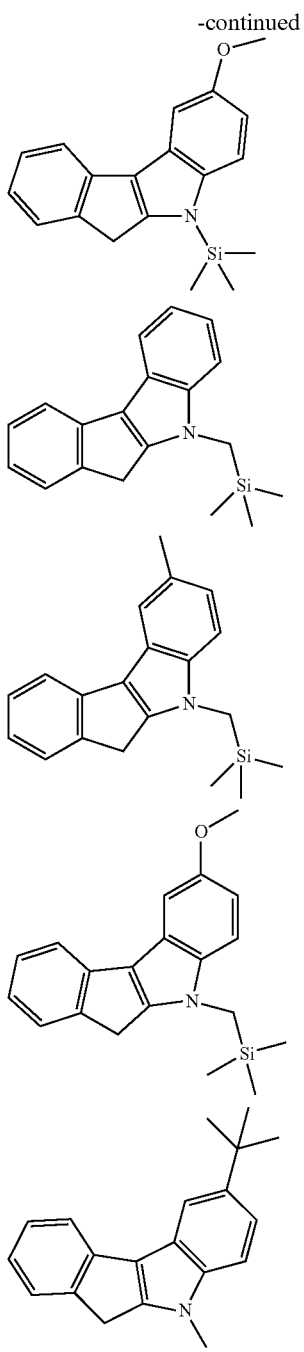
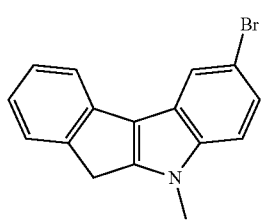
-continued
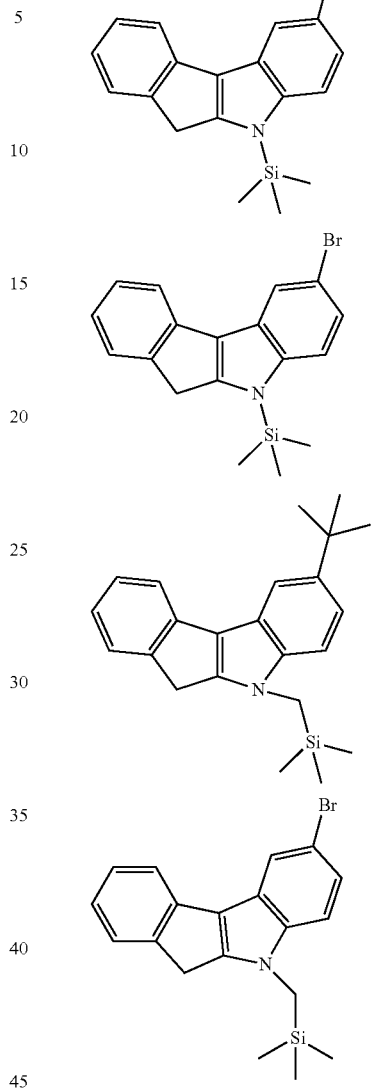
Further, a specific example of the structure represented by Chemical Formula 7c may be a structure represented by any one of the following structural formulae, but is not limited thereto.
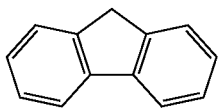
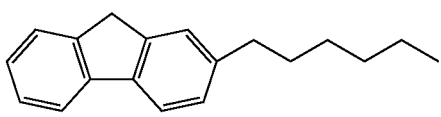
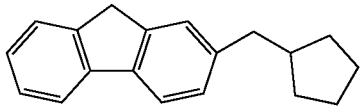

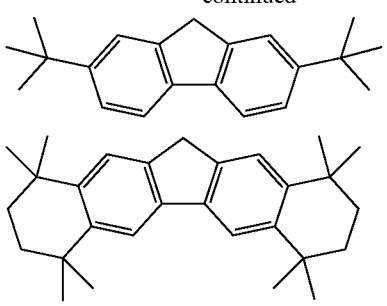
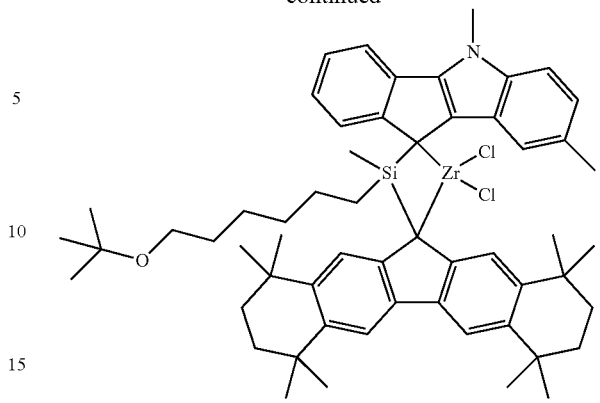
Additionally, a specific example of the metallocene compound represented by Chemical Formula 6 may be a compound represented by any one of the following structural formulae, but is not limited thereto.
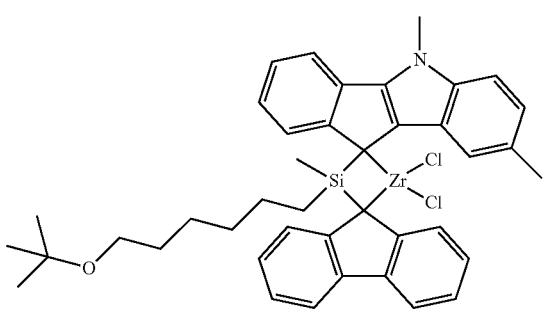
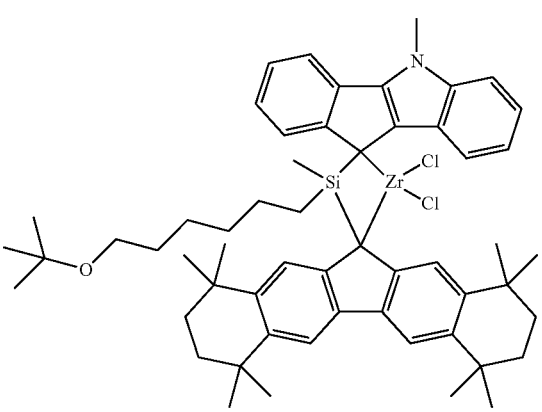
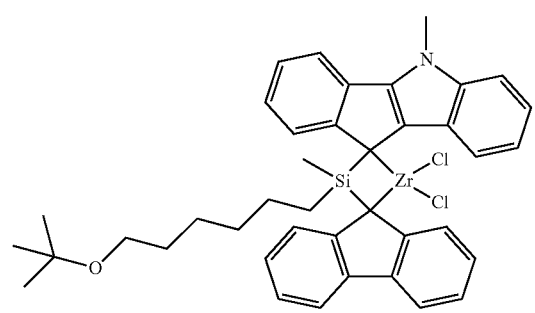
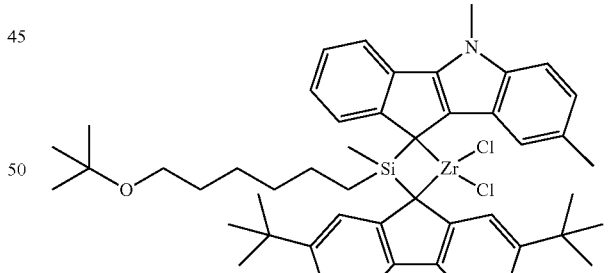
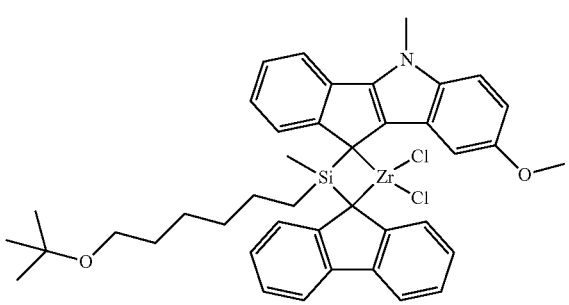
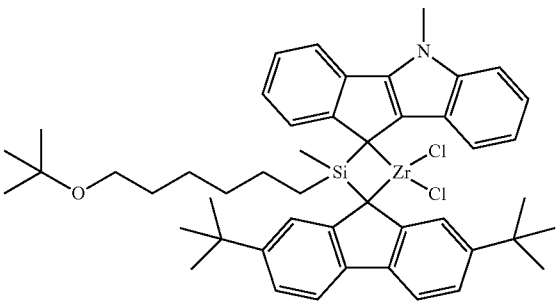

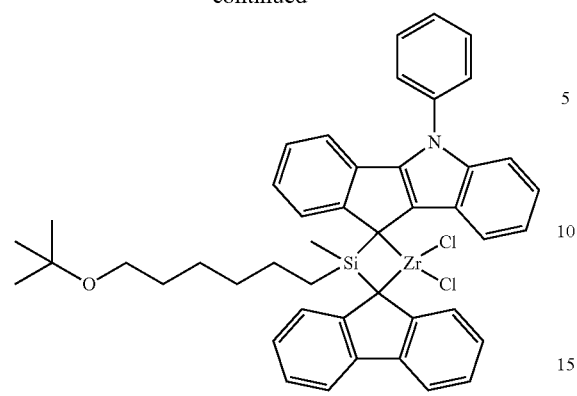
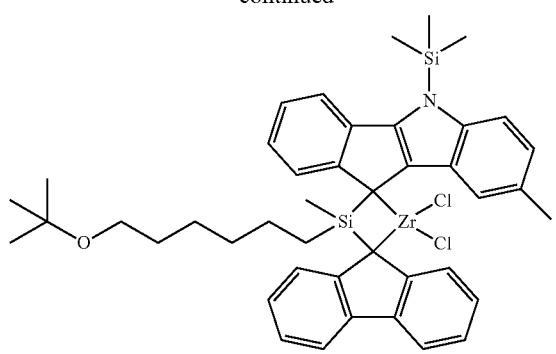
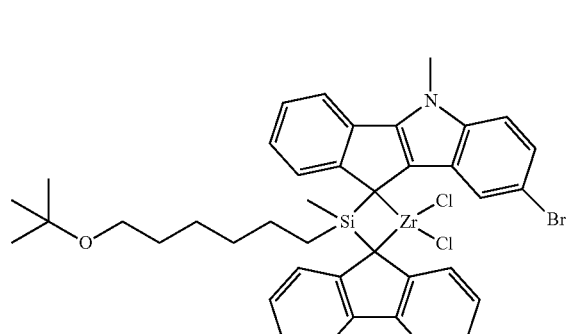
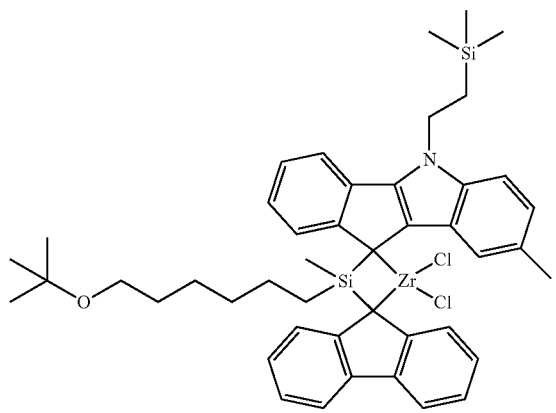
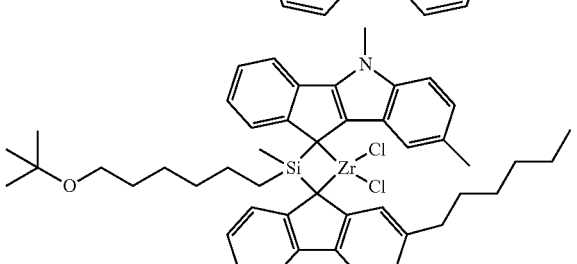
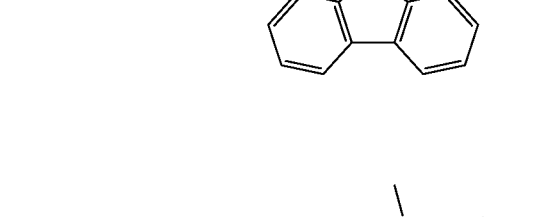
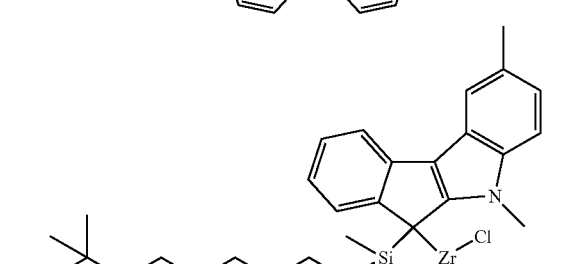
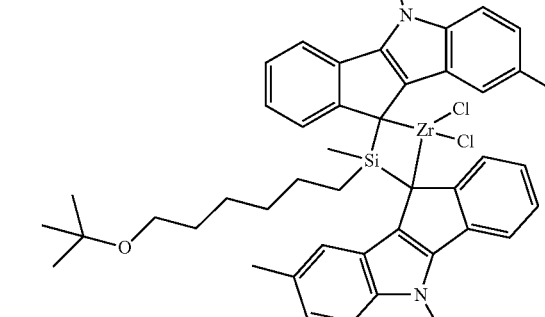
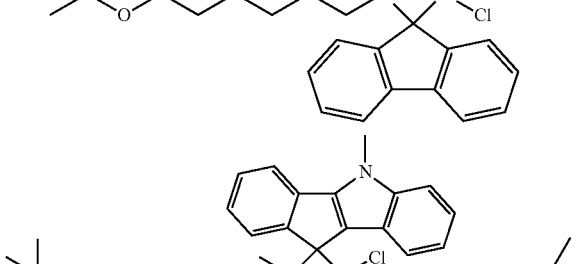
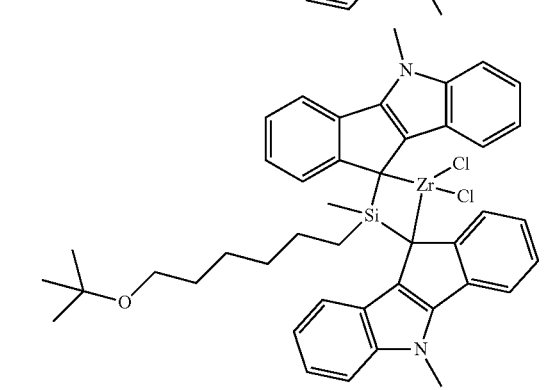

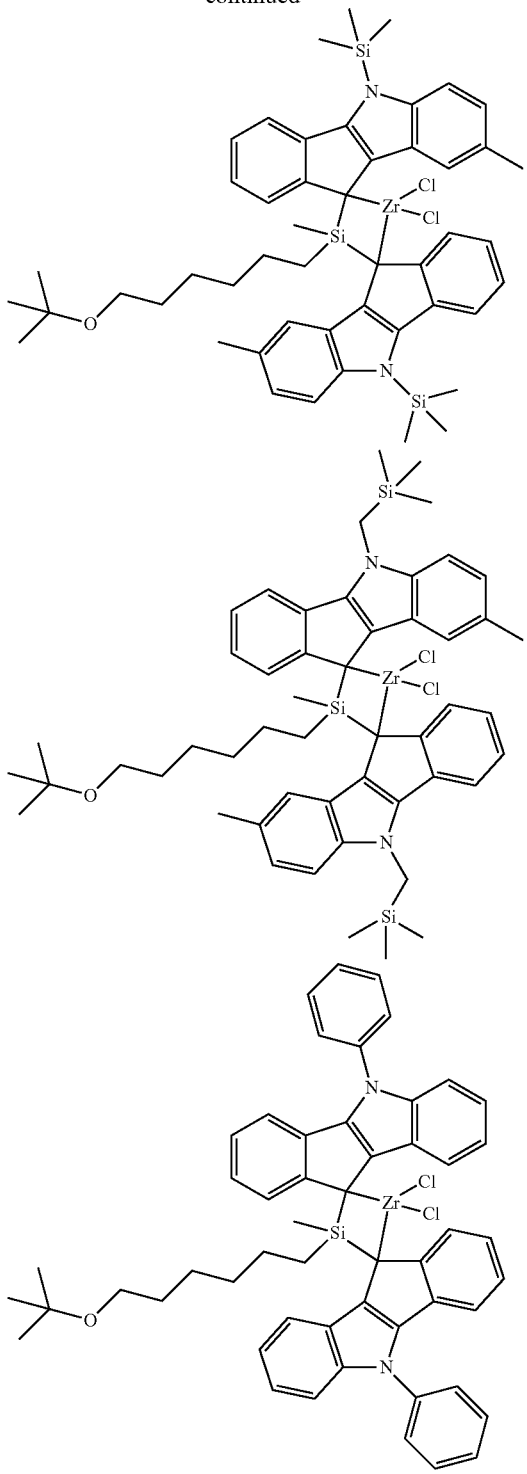

The metallocene compound of Chemical Formula 6 may be obtained by linking the indeno indole derivative and/or the fluorene derivative via a bridge compound to prepare a ligand compound, and then injecting a metal precursor compound thereto to perform metallation, but is not limited thereto.

In the preparation method of an embodiment, the above-described metallocene compound and molecular weight modifier composition are used in the form of a supported catalyst prepared by supporting them on a support. The supporting may be performed by mixing the support, the metallocene catalyst, and the molecular weight modifier composition, and stirring a resulting mixture at a temperature of 30° C. to 100° C., preferably 35° C. to 90° C., or 40° C. to 80° C. for 1 h to 12 h, preferably 1 h to 4 h.

Meanwhile, the supported metallocene catalyst may be used in the form of a supported metallocene catalyst in which the metallocene compound and a cocatalyst are supported on a support, for example, in the form of a hybrid supported metallocene catalyst including two or more different metallocene compounds and the cocatalyst.

In this regard, the support may be silica, silica-alumina, silica-magnesia, etc. Any support known to support metallocene catalysts may be used. Further, a support dried at a high temperature may be used, and the drying temperature may be, for example, about 180° C. to 800° C. If the drying temperature is too low, an excessive amount of water on the support reacts with the cocatalyst to reduce performance, and if the drying temperature is too high, an amount of a hydroxyl group on the support surface becomes too low to reduce a reactive site with the cocatalyst.

In particular, the support may be one on which a first aluminum-containing cocatalyst of the following Chemical Formula 12 is supported:

$$-[-Al(R^{18})-O-]_n-$$ 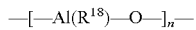 Chemical Formula 12 in Chemical Formula 12, each $R^{18}$ is independently a halogen, or a halogen-substituted or unsubstituted hydrocarbyl having 1 to 20 carbon atoms, and n is an integer of 2 or more.

In the present invention, the molecular weight modifier composition may be supported immediately after supporting the metallocene compound on the first cocatalyst-supported support. According to the prior technology, organic aluminum in MAO and the precursor are first reacted, and then supported on silica. First, titanocene is added to an MAO solution to allow an in-situ Tebbe reagent reaction of titanocene and TMA in MAO, and this Tebbe material thus obtained, that is, Tebbe reagent in MAO, may react with the precursor due to a high temperature upon being supported on silica. However, this method of preparing the supported catalyst is problematic in that non-uniformity of a MAO solution due to the reaction between the precursor and MAO may cause a reduction in stability of the supported catalyst, and a short reaction time of the known Tebbe reagent, compared to about 2 days to 4 days, e.g., 3 days of the present invention, may cause reproducibility problems of the catalyst characteristics.

Particularly, in the present invention, uniformity of silica-MAO itself may be secured by injecting the molecular weight modifier immediately after injecting the metallocene compound catalyst precursor to the first cocatalyst (e.g., MAO, etc.)—supported silica, and a sufficient increase of the molecular weight may be obtained using the molecular weight modifier even in a catalytic amount relative to the precursor. Further, the present invention may prevent a reduction in the intrinsic activity of the precursor, because the small amount of the molecular weight modifier is used.

Meanwhile, the above-described metallocene catalyst, particular, the hybrid supported metallocene catalyst, may further include a second borate-based cocatalyst of the following Chemical Formula 13:

$$T^+[BQ_4]^-$$  Chemical Formula 13 in Chemical Formula 13, $T^+$ is a positive monovalent (+1) polyatomic ion, B is boron having an oxidation state of +3, and each Q is independently selected from the group consisting of a hydride group, a dialkylamido group, a halide group, an alkoxide group, an aryloxide group, a hydrocarbyl group, a halocarbyl group, and a halo-substituted hydrocarbyl group, in which Q has 20 or fewer carbon atoms, provided that only one or fewer of Q is a halide group.

The final polyolefin prepared by using the first and second cocatalysts may have a more uniform molecular weight distribution, thereby improving the polymerization activity.

The first cocatalyst of Chemical Formula 12 may have a linear, circular, or net shape, and it may be an alkylaluminoxane-based compound having a repeating unit. Specific examples of the first cocatalyst may include methylaluminoxane (MAO), ethylaluminoxane, isobutylaluminoxane, butylaluminoxane, etc.

Further, the second cocatalyst of Chemical Formula 13 may be a borate-based compound in the form of a tri-substituted ammonium salt, a dialkyl ammonium salt, or a tri-substituted phosphonium salt. Specific examples of the second cocatalyst may include a borate-based compound in the form of a tri-substituted ammonium salt, such as trimethylammonium tetraphenylborate, methyldioctadecylammonium tetraphenylborate, triethylammonium tetraphenylborate, tripropylammonium tetraphenylborate, tri(n-butyl) ammonium tetraphenylborate, methyltetradecyclooctadecylammonium tetraphenylborate, N,N-dimethylanilinium tetraphenylborate, N,N-diethylanilinium tetraphenylborate, N,N-dimethyl(2,4,6-trimethylanilinium)tetraphenylborate, trimethylammonium tetrakis(pentafluorophenyl)borate, methylditetradecylammonium tetrakis(pentaphenyl)borate, methyldioctadecylammonium tetrakis(pentafluorophenyl)borate, triethylammonium, tetrakis(pentafluorophenyl)borate, tripropylammoniumtetrakis(pentafluorophenyl)borate, tri(n-butyl)ammonium tetrakis(pentafluorophenyl)borate, tri(sec-butyl)ammoniumtetrakis(pentafluorophenyl)borate, N,N-dimethylanilinium tetrakis(pentafluorophenyl)borate, N,N-diethylaniliniumtetrakis(pentafluorophenyl)borate, N,N-dimethyl(2,4,6-trimethylanilinium)tetrakis(pentafluorophenyl)borate, trimethylammoniumtetrakis(2,3,4,6-tetrafluorophenyl)borate, triethylammonium tetrakis(2,3,4,6-tetrafluorophenyl)borate, tripropylammonium tetrakis(2,3,4,6-tetrafluorophenyl)borate, tri(n-butyl)ammonium tetrakis(2,3,4,6-tetrafluorophenyl)borate, dimethyl(t-butyl)ammonium tetrakis(2,3,4,6-tetrafluorophenyl)borate, N,N-dimethylanilinium tetrakis(2,3,4,6-tetrafluorophenyl)borate, N,N-diethylanilinium tetrakis(2,3,4,6-tetrafluorophenyl)borate or N, N-dimethyl-(2,4,6-trimethylanilinium)tetrakis-(2,3,4,6-tetrafluorophenyl)borate, etc.; a borate-based compound in the form of a dialkylammonium salt, such as dioctadecylammonium tetrakis(pentafluorophenyl)borate, ditetradecylammonium tetrakis(pentafluorophenyl)borate, dicyclohexylammonium tetrakis(pentafluorophenyl)borate, etc.; a borate-based compound in the form of a tri-substituted phosphonium salt, such as triphenylphosphonium tetrakis(pentafluorophenyl)borate, methyldioctadecylphosphonium tetrakis(pentafluorophenyl)borate, tri(2,6-dimethylphenyl)phosphonium tetrakis(pentafluorophenyl)borate, etc.

When the hybrid supported metallocene catalyst is prepared by using the first and second metallocene compounds of two or more of the above-described metallocene compounds and the first and second cocatalysts, it is preferable for the first metallocene compound and the first cocatalyst to be serially supported on the support, and subsequently, the second metallocene compound and the second cocatalyst may be serially supported. A washing step may be additionally performed by using a solvent between the supporting steps.

According to another embodiment of the present invention, a method of preparing a polyolefin is provided, the method including polymerizing olefinic monomers in the presence of the above-described supported metallocene catalyst, in which the metallocene compound and the particular molecular weight modifier are supported on the support.

The polymerizing of olefinic monomers may be performed by slurry polymerization of olefinic monomers in the presence of the supported metallocene catalyst which is obtained by supporting one or more metallocene compounds represented by any one of Chemical Formulae 3 to 6 on a support, together with the molecular weight modifier composition which is obtained by mixing the cyclopentadienyl metal compound of Chemical Formula 1 and the organic aluminum compound of Chemical Formula 2 and then stirring a resulting mixture at room temperature, for example, at 22.5° C. to 25° C. for 50 h to 108 h, preferably 62 h to 90 h.

In the method of preparing the polyolefin according to an embodiment, the polyolefin may be prepared by polymerizing arbitrary olefinic monomers. In this regard, specific examples of the useable olefinic monomer may include ethylene, propylene, 1-butene, 1 pentene, 4-methyl-1-pentene, 1-hexene, 1-heptene, 1-octene, 1-decene, 1-undencene, 1-dodecene, 1-tetradecene, 1-hexadecene, 1-eicosene, norbornene, norbornadiene, ethylidenenorbomene, phenylnorbomene, vinylnorbomene, dicyclopentadiene, 1,4-butadiene, 1,5-pentadiene, 1,6-hexadiene, styrene, alpha-methylstyrene, divinylbenzene, 3-chloromethylstyrene, etc. However, in an example of the preparation method, ethylene is used to prepare polyethylene, or ethylene is copolymerized with an alpha-olefin such as propylene, 1-butene, 1-hexene, 1-octene, 1-pentene, 4-methyl-1-pentene, 1-hexene, 1-heptene, 1-decene, 1-undecene, 1-dodecene, etc. to prepare an ethylene-alpha olefin copolymer. In this regard, the comonomer such as the alpha-olefin may be copolymerized by using the comonomer in an amount of about 30% by weight or less, about 0% by weight to about 20% by weight, or about 0.1% by weight to about 15% by weight with respect to the total content of olefinic monomers. As this amount of alpha-olefin is used for copolymerization, the final polyolefin may exhibit excellent stress-cracking resistance within the density range suitable for blow-molding. However, if an excessively large amount of alpha-olefin is used, density of the polymer may be decreased to cause a reduction in flexural strength.

Additionally, the above-described polymerization method of an embodiment may be performed, for example, in an aliphatic hydrocarbon-based solvent such as hexane, butane, pentane, etc. by slurry phase polymerization. Since the metallocene catalyst including the molecular weight modifier exhibits excellent solubility for the solvent, they may be stably solubilized and fed into a reaction system to allow an effective polymerization process and to effectively prepare a polyolefin having a high molecular weight and a broader molecular weight distribution.

The above-described polymerization method of an embodiment may be carried out by homopolymerizing one kind of olefinic monomer or by copolymerizing two or more kinds of monomers, using a continuous slurry polymerization reactor, a loop slurry reactor, a gas phase reactor, or a solution reactor.

The polymerization of the olefinic monomers may be carried out at a temperature of about 25° C. to about 500° C. and at a reaction pressure of about 1 kgf/cm² to about 100 kgf/cm² for about 1 h to about 24 h. Specifically, the polymerization of the olefinic monomers may be carried out at a temperature of about 25° C. to about 500° C., preferably at about 25° C. to about 200° C., and more preferably at about 50° C. to about 100° C. Further, the polymerization may be carried out at a reaction pressure of about 1 kgf/cm² to about 100 kgf/cm², preferably at about 1 kgf/cm² to about 50 kgf/cm², and more preferably at about 5 kgf/cm² to about 40 kgf/cm².

According to the present invention, the molecular weight of the polymer may be effectively increased and high activity may also be maintained during olefin polymerization. In the method of preparing the polyolefin of the present invention, particularly, the catalytic activity may be 1.0 kg/gCat·h or more, or 1.0 to 15.0 kg/gCat·h, preferably 10.0 kg/gCat·h or more, and more preferably 8.0 kg/gCat·h, as calculated by a ratio of the weight (kg) of the produced polymer per the weight (g) of the used catalyst per unit time (h).

Particularly, in the present invention, although the molecular weight modifier is used in a small amount corresponding to the catalytic amount of the metallocene precursor which is supported during preparation of the supported metallocene catalyst, a molecular weight of the single or hybrid supported catalyst may be effectively controlled. The prior technologies are characterized by simply increasing the molecular weight, whereas the present invention is advantageous in that a polymer structure may be finely controlled according to an amount of the molecular weight modifier while maintaining polymerization conditions where no activity reduction occurs.

According to still another embodiment of the present invention, a polyolefin prepared according to the above-described preparation method of an embodiment is provided. This polyolefin may be preferably used for blow molding, injection molding, etc., because its molecular weight distribution is such that the molecular weight and polymer elasticity are increased to improve swell.

Owing to the action of the above-described molecular weight modifier, the polyolefin according to the present invention may have a high molecular weight of about 100,000 to about 2,000,000, or about 110,000 to about 1,500,000, about 120,000 to about 700,000, about 150,000 to about 550,000, or about 200,000 to about 450,000, and may have a molecular weight distribution whereby polymer elasticity is increased to improve swell. When the polyolefin is prepared by slurry polymerization, the polyolefin may have a much higher molecular weight of about 250,000 or higher, about 280,000 or higher, about 300,000 or higher, or about 330,000 or higher. Further, the polyolefin prepared by slurry polymerization may have a melt index (MI 21.6 kg) of 15.0 g/10 min or less, or 0.01 to 15 g/10 min, preferably 10 g/10 min or less, and more preferably 1 g/10 min or less. Due to the molecular weight distribution whereby the molecular weight and polymer elasticity are increased to improve swell, the polyolefin may exhibit excellent mechanical properties and processability at the same time. In particular, according to the present invention, a polyolefin having excellent mechanical properties such as ESCR (Environmental Stress-Cracking Resistance), low-temperature impact resistance, etc. may be prepared due to the high molecular weight. Such a polyolefin may be used for blow-molding, and may be applied to injection molding, films, pipes, bottle caps, etc.

Effect of the Invention

As described above, according to the present invention, a method of preparing a supported metallocene catalyst capable of more effectively preparing a polyolefin which may be preferably used for blow molding, injection molding, etc., because its molecular weight distribution is such that a molecular weight and polymer elasticity are increased to improve swell, is provided.

The supported metallocene catalyst may be used to very effectively prepare a polyolefin which has a low melt index, a broad molecular weight distribution, and high stress cracking resistance (Full Notch Creep Test; FNCT), considering density or melt index, and therefore is particularly suitable for blow-molding, injection molding, etc.

DETAILED DESCRIPTION OF THE EMBODIMENTS

Figure 1:
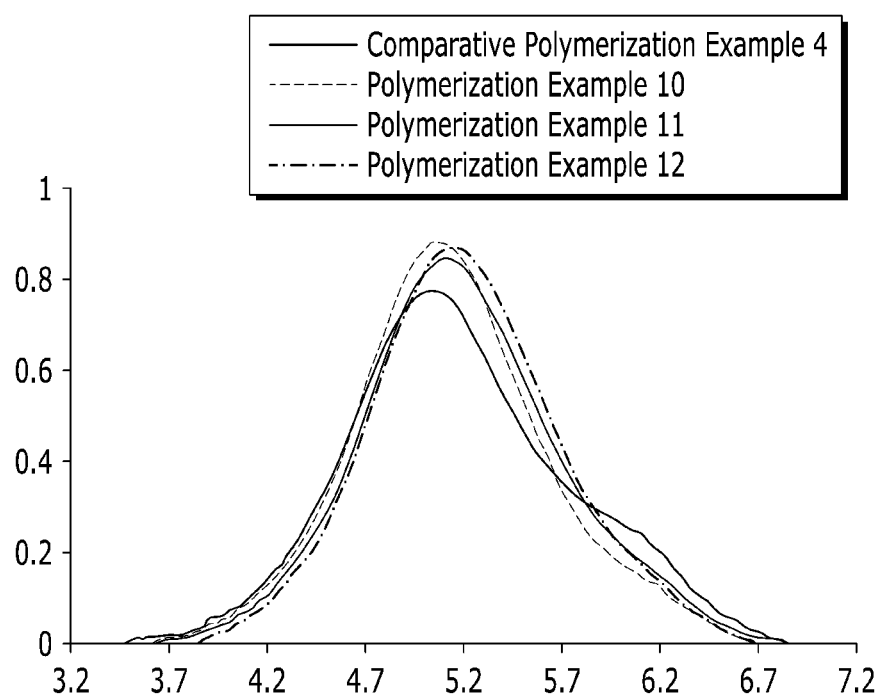
FIG. 1 is a graph showing molecular weight distributions of polymers which were polymerized by using supported metallocene catalysts prepared in Examples 10 to 12 and Comparative Example 4 (brown: Polymerization Example 10, red: Polymerization Example 11, purple: Polymerization Example 12, blue: Comparative Polymerization Example 4)

Hereinafter, preferred examples are provided for better understanding. However, the following examples are for illustrative purposes only, and the scope of the present invention is not intended to be limited by the following examples.

EXAMPLES

Preparation Example of Metallocene Catalyst Precursor

Synthesis Example 1 Synthesis of [t-Bu-O(CH$_2$)$_6$—C$_5$H$_4$]$_2$ZrMe$_2$

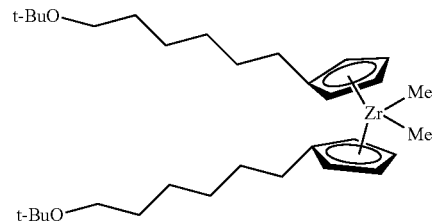

t-butyl-O—(CH$_2$)$_6$—Cl was prepared using 6-chlorohexanol according to a method described in the document (*Tetrahedron Lett.* 2951 (1988)), and reacted with NaC$_5$H$_5$ to obtain t-butyl-O—(CH$_2$)$_6$—C$_5$H$_5$(yield: 60%, b.p. 80° C./0.1 mmHg). 2.0 g (9.0 mmol) of t-butyl-O—(CH$_2$)$_6$—C$_5$H$_5$ was dissolved in THF at −78° C., and 1.0 equivalent weight of normal butyl lithium (n-BuLi) was slowly added thereto. The temperature was raised to room temperature, and reaction was allowed for 8 h. This reaction solution was slowly added to a suspension solution of Zr(CH$_3$)$_2$(THF)$_2$ (1.70 g, 4.50 mmol)/THF (30 mL) at −78° C., and then further reacted at room temperature for 6 h to obtain a final reaction solution.

The reaction solution was dried under vacuum to remove all volatile materials, and then hexane was added to a remaining oily liquid, followed by filtration using a Schlenk glass filter. A filtrate solution was dried under vacuum to remove hexane, and then hexane was added thereto to induce precipitation at a low temperature (−20° C.). A resulting precipitate was filtered at a low temperature to obtain a [t-Bu-O(CH$_2$)$_6$—C$_5$H$_4$]$_2$ZrCl$_2$ compound as a white solid with a yield of 92%. $^1$H NMR and $^{13}$C NMR data of [t-Bu-O(CH$_2$)$_6$—C$_5$H$_4$]$_2$ZrCl$_2$ thus obtained are as follows.

$^1$H NMR (300 MHz, CDCl$_3$): 6.28 (t, J=2.6 Hz, 2H), 6.19 (t, J=2.6 Hz, 2H), 3.31 (t-J=6.6 Hz, 2H), 2.62 (t, J=8 Hz, 2H), 1.7-1.3 (m, 8H), 1.17 (s, 9H)

$^{13}$C NMR (CDCl$_3$): 135.09, 116.66, 112.28, 72.42, 61.52, 30.66, 30.61, 30.14, 29.18, 27.58, 26.00

Synthesis Example 2 Synthesis of 2(t-Bu-O—(CH$_2$)$_6$)(CH$_3$)Si(C$_5$(CH$_3$)$_4$)(tBu-N)TiCl$_2$)

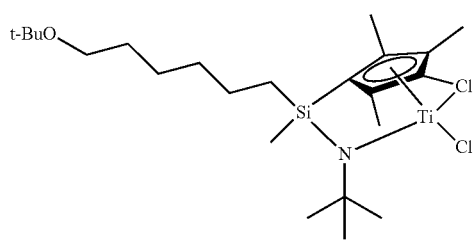

50 g of Mg(s) was added to a 10 L reactor at room temperature, and then 300 mL of THF was added thereto.

About 0.5 g of I$_2$ was added, and the reactor temperature was maintained at 50° C. After the reactor temperature was stabilized, 250 g of 6-t-butoxyhexyl chloride was added to the reactor by using a feeding pump at a speed of 5 mL/min. According to the addition of 6-t-butoxyhexyl chloride, it was observed that the reactor temperature was increased by about 4° C. to 5° C. While 6-t-butoxyhexyl chloride was continuously added, agitation was performed for 12 h.

A black reaction solution was obtained after reaction for 12 h. After 2 mL of the formed black solution was sampled, water was added thereto to obtain an organic layer. 6-t-butoxyhexane was confirmed by $^1$H-NMR. 6-t-butoxyhexane indicates that a Grignard reaction occurred well. Accordingly, 6-t-butoxyhexyl magnesium chloride was synthesized.

500 g of MeSiCl$_3$ and 1 L of THF were added to a reactor, and the reactor temperature was cooled to −20° C. 560 g of the synthesized 6-t-butoxyhexyl magnesium chloride was added to the reactor by using the feeding pump at a speed of 5 mL/min.

After injection of the Grignard reagent was finished, the reactor temperature was slowly raised to room temperature and agitation was performed for 12 h.

After reaction for 12 h, it was confirmed that a white MgCl$_2$ salt was generated. 4 L of hexane was added and the salt was removed through a labdori to obtain a filter solution.

After the filter solution was added to the reactor, hexane was removed at 70° C. to obtain a light yellow liquid.

The obtained liquid was identified as a desired methyl(6-t-butoxyhexyl)dichlorosilane compound by $^1$H-NMR.

$^1$H-NMR (CDCl$_3$): δ=3.3 (t, 2H), 1.5 (m, 3H), 1.3 (m, 5H), 1.2 (s, 9H), 1.1 (m, 2H), 0.7 (s, 3H)

1.2 mol of tetramethylcyclopentadiene (150 g) and 2.4 L of THF were added to the reactor, and the reactor temperature was cooled to −20° C. 480 mL of n-BuLi was added to the reactor by using the feeding pump at a speed of 5 mL/min. After n-BuLi was added, the reactor temperature was slowly raised to room temperature and agitation was performed for 12 h. After reaction for 12 h, an equivalent amount of methyl(6-t-butoxy hexyl)dichlorosilane (326 g, 350 mL) was rapidly added to the reactor. The reactor temperature was slowly raised to room temperature and agitation was performed for 12 h. After reaction for 12 hrs, THF was removed, and 4 L of hexane was added and salts were removed through a labdori to obtain a filter solution. After the filter solution was added to the reactor, hexane was removed at 70° C. to obtain a yellow liquid. The obtained yellow liquid was identified as a desired methyl(6-t-butoxyhexyl)(tetramethylCpH)t-butylaminosilane compound by $^1$H-NMR.

TiCl$_3$(THF)$_3$ (10 mmol) was rapidly added to n-BuLi and a dilithium salt of the ligand at −78° C., which was synthesized from a ligand dimethyl(tetramethylCpH)t-butylaminosilane in a THF solution. This reaction solution was agitated for 12 h while the temperature was slowly increased from −78° C. to room temperature.

After agitation for 12 h, an equivalent amount of PbCl$_2$ (10 mmol) was added to the reaction solution at room temperature, followed by agitation for 12 h. After agitation for 12 h, a dark black solution with a blue tinge was obtained. After THF was removed from the generated reaction solution, hexane was added to filter a product. After hexane was removed from a filter solution, the solution was identified as a desired [methyl(6-t-butoxyhexyl)silyl(5-tetramethylCp)(t-butylamido)]TiCl$_2$ compound by $^1$H-NMR.

$^1$H-NMR (CDCl$_3$): δ=3.3 (s, 4H), 2.2 (s, 6H), 2.1 (s, 6G), 1.8 to 0.8 (m), 1.4 (s, 9H), 1.2 (s, 9H), 0.7 (3, 3H)

Synthesis Example 3

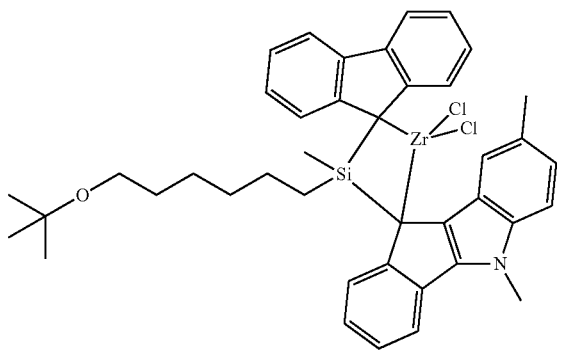

3-1 Preparation of Ligand Compound 2 g of fluorene was dissolved in 5 mL of MTBE and 100 mL of hexane, and then 5.5 mL of a 2.5 M, n-BuLi hexane solution was added dropwise thereto in a dry ice/acetone bath, followed by agitation at room temperature overnight. 3.6 g of (6-(tert-butoxy)hexyl)dichloro(methyl)silane was dissolved in 50 mL of hexane, and a fluorene-Li slurry was transferred in a dry ice/acetone bath for 30 min, followed by agitation at room temperature overnight. Simultaneously, 5,8-dimethyl-5,10-dihydroindeno [1,2-b]-indole (12 mmol, 2.8 g) was also dissolved in 60 mL of THF, and 5.5 mL of a 2.5 M, n-BuLi hexane solution was added dropwise thereto in a dry ice/acetone bath, followed by agitation at room temperature overnight. NMR sampling of a reaction solution of fluorene and (6-(tert-butoxy)hexyl)dichloro(methyl)silane was performed to confirm completion of the reaction, and then a 5,8-dimethyl-5,10-dihydroindeno [1,2-b]-indole-Li solution was transferred in a dry ice/acetone bath. The mixture was agitated at room temperature overnight. After reaction, extraction was performed using ether/water, and remaining water of an organic layer was dried over $MgSO_4$ to obtain a ligand compound (Mw 597.90, 12 mmol). Production of two isomers was confirmed by $^1$H-NMR.

$^1$H NMR (500 MHz, d6-benzene): −0.30-−0.18 (3H, d), 0.40 (2H, m), 0.65-1.45 (8H, m), 1.12 (9H, d), 2.36-2.40 (3H, d), 3.17 (2H, m), 3.41-3.43 (3H, d), 4.17-4.21 (1H, d), 4.34-4.38 (1H, d), 6.90-7.80 (15H, m)

3-2 Preparation of Metallocene Compound 7.2 g (12 mmol) of the ligand compound prepared in 3-1 was dissolved in 50 mL of diethylether, and 11.5 mL of a 2.5 M, n-BuLi hexane solution was added dropwise thereto in a dry ice/acetone bath, followed by agitation at room temperature overnight. The solution was dried under vacuum to obtain a brown sticky oil, which was dissolved in toluene to obtain a slurry. $ZrCl_4(THF)_2$ was prepared, and 50 mL of toluene was added thereto to prepare a slurry. 50 mL of the toluene slurry of $ZrCl_4(THF)_2$ was transferred in a dry ice/acetone bath, followed by agitation at room temperature overnight. The solution changed to a violet color. This reaction solution was filtered to remove LiCl. Toluene was removed from a filtrate by drying under vacuum, and then hexane was added thereto, followed by sonication for 1 h. A slurry was filtered, and a filtered solid was 6 g of a dark violet metallocene compound (Mw 758.02, 7.92 mmol, yield 66 mol %). Two isomers were observed in $^1$H-NMR.

$^1$H NMR (500 MHz, $CDCl_3$): 1.19 (9H, d), 1.71 (3H, d), 1.50-1.70 (4H, m), 1.79 (2H, m), 1.98-2.19 (4H, m), 2.58 (3H, s), 3.38 (2H, m), 3.91 (3H, d), 6.66-7.88 (15H, m)

Preparation Example of Molecular Weight Modifier

Synthesis Example 4: Preparation of Molecular Weight Modifier

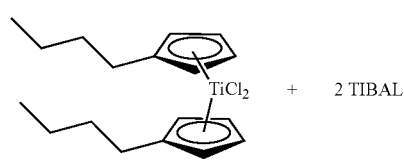

1.08 g (3 mmol) of bis(2-butylcyclopenta-2,4-dien-1-yl)titanium(IV) chloride was placed in a 250 mL round bottom flask, and 50 mL of hexane was added thereto, followed by agitation. 6 mL (6 mmol) of triisobutyl aluminum (1 M in hexane) was added thereto, followed by agitation at room temperature for 3 days. The solvent was removed under vacuum to obtain a blue liquid mixture. Since this mixture was under reduction of titanium, it was not oxidized or color-changed. The blue mixture was used as is without purification, as below.

$^1$H NMR ($CDCl_3$, 500 MHz): 6.1-6.6 (br m, 8H), 2.2 (m, 4H), 1.0-1.8 (br m, 16H), 0.4 (br s, 24H)

Synthesis Example 5: Preparation of Molecular Weight Modifier

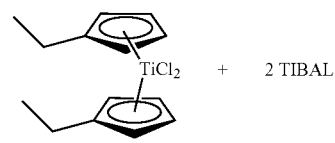

0.91 g (3 mmol) of bis(2-ethylcyclopenta-2,4-dien-1-yl)titanium(IV) chloride was placed in a 250 mL round bottom flask, and 50 mL of hexane was added thereto, followed by agitation. 6 mL (6 mmol) of triisobutyl aluminum (1 M in hexane) was added thereto, followed by agitation at room temperature for 3 days. The solvent was removed under vacuum to obtain a blue liquid mixture. Since this mixture was under reduction of titanium, it was not oxidized or color-changed. The blue mixture was used as is without purification, as below.

$^1$H NMR ($CDCl_3$, 500 MHz): 6.2-6.6 (br m, 8H), 1.0-1.8 (br m, 7H), 0.8 (br s, 24H)

Synthesis Example 6: Preparation of Molecular Weight Modifier

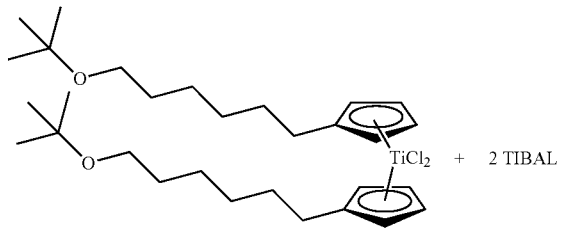

1.68 g (3 mmol) of bis(2-(6-t-butoxy-hexyl)cyclopenta-2,4-dien-1-yl)titanium(IV) chloride was placed in a 250 mL round bottom flask, and 50 mL of hexane was added thereto, followed by agitation. 6 mL (6 mmol) of triisobutyl aluminum (1 M in hexane) was added thereto, followed by agitation at room temperature for 3 days. The solvent was removed under vacuum to obtain a blue liquid mixture. Since this mixture was under reduction of titanium, it was not oxidized or color-changed. The blue mixture was used as is without purification, as below.

$^1$H NMR ($CDCl_3$, 500 MHz): 6.31 (br m, 8H), 3.5 (m, 4H), 1.1-1.9 (br m, 28H), 0.9 (br s, 18H), 0.3 (br s, 18H)

Synthesis Example 7: Preparation of Molecular Weight Modifier

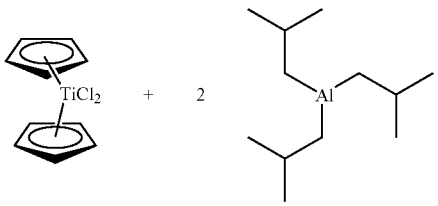

0.83 g of bis(cyclopentadienyl)-titanium dichloride and 50 mL of hexane were serially placed in a 250 mL round bottom flask, followed by agitation. 6 mL of triisobutyl aluminum (1 M in hexane) was added thereto, followed by agitation at room temperature for 3 days. The solvent was removed under vacuum to obtain a green mixture. Since this mixture was under reduction of titanium, it was not oxidized or color-changed. The green mixture was used as is without purification, as below.

$^1$H NMR (CDCl$_3$, 500 MHz): 6.3-6.6 (br m, 10H), 1.2-1.8 (br m, 4H), 0.8 (br s, 18H)

Preparation Example of Supported Metallocene Catalyst

Example 1: Preparation of Supported Metallocene Catalyst

First, silica (SYLOPOL 948 manufactured by Grace Davison, Co., Ltd.) was dehydrated under vacuum at 400° C. for 15 h.

49.7 mL of 10 wt % methylaluminoxane(MAO)/toluene solution was added to a glass reactor, and 9.1 g of silica (SYLOPOL 948 manufactured by Grace Davison, Co., Ltd.) was added thereto at 40° C., followed by agitation while raising the reactor temperature to 80° C. Thereafter, the temperature was maintained at 80° C., and 550 mg (0.1 mmol/g SiO$_2$) of the catalyst precursor prepared in Synthesis Example 1 was dissolved in 20 mL of toluene and immediately added to the reactor, together with 53 mg (10 mol % of the precursor) of the molecular weight modifier prepared in Synthesis Example 4. After agitation for 2 h, 948 mg (0.12 mmol/g SiO$_2$) of anilinium borate (N,N-dimethylanilinium tetrakis(pentafluorophenyl)borate, AB) previously dissolved in 20 mL of toluene was added in a solution state, followed by agitation at 40° C. for 2 h. After reaction was completed, agitation was stopped and a toluene layer was separated and removed. Remaining toluene was removed under reduced pressure at 40° C. to prepare a supported metallocene catalyst.

Examples 2 and 3: Preparation of Supported Metallocene Catalyst

Supported metallocene catalysts were prepared in the same manner as in Example 1, except that the molecular weight modifier was added in an amount of 160 mg (30 mol %) and 270 mg (50 mol %) as shown in the following Table 1.

Example 4: Preparation of Supported Metallocene Catalyst

A supported metallocene catalyst was prepared in the same manner as in Example 1, except that 465 mg (0.1 mmol/g SiO$_2$) of the catalyst precursor prepared in Synthesis Example 2 was used as shown in the following Table 1.

Examples 5 and 6: Preparation of Supported Metallocene Catalyst

Supported metallocene catalysts were prepared in the same manner as in Example 4, except that the molecular weight modifier was added in an amount of 160 mg (30 mol %) and 270 mg (50 mol %) as shown in the following Table 1.

Example 7: Preparation of Supported Metallocene Catalyst

A supported metallocene catalyst was prepared in the same manner as in Example 1, except that 690 mg (0.1 mmol/g SiO$_2$) of the catalyst precursor prepared in Synthesis Example 3 was used as shown in the following Table 1.

Examples 8 and 9: Preparation of Supported Metallocene Catalyst

Supported metallocene catalysts were prepared in the same manner as in Example 7, except that the molecular weight modifier was added in an amount of 160 mg (30 mol %) and 270 mg (50 mol %) as shown in the following Table 1.

Example 10: Preparation of Supported Metallocene Catalyst

First, silica (SYLOPOL 948 manufactured by Grace Davison, Co., Ltd.) was dehydrated under vacuum at 400° C. for 15 h.

49.7 mL of 10 wt % methylaluminoxane(MAO)/toluene solution was added to a glass reactor, and 9.1 g of silica (SYLOPOL 948 manufactured by Grace Davison, Co., Ltd.) was added thereto at 40° C., followed by agitation while raising the reactor temperature to 80° C. Thereafter, the temperature was maintained at 80° C., and 520 mg (0.075 mmol/g SiO$_2$) of the catalyst precursor prepared in Synthesis Example 3 was dissolved in 20 mL of toluene and immediately added to the reactor, together with 53 mg (10 mol % of the precursor) of the molecular weight modifier prepared in Synthesis Example 4. After agitation for 2 h, 550 mg (0.1 mmol/g SiO$_2$) of the catalyst precursor prepared in Synthesis Example 1 was reacted at 40° C. for 2 h, and then 948 mg (0.12 mmol/g SiO$_2$) of anilinium borate (N,N-dimethylanilinium tetrakis(pentafluorophenyl)borate, AB) previously dissolved in 20 mL of toluene was added in a solution state, followed by agitation at 40° C. for 2 h. After reaction was completed, agitation was stopped and a toluene layer was separated and removed. Remaining toluene was removed under reduced pressure at 40° C. to prepare a supported metallocene catalyst.

Examples 11 and 12: Preparation of Supported Metallocene Catalyst

Supported metallocene catalysts were prepared in the same manner as in Example 10, except that the molecular weight modifier was added in an amount of 160 mg (30 mol %) and 270 mg (50 mol %) as shown in the following Table 1.

Comparative Example 1: Preparation of Supported Metallocene Catalyst

First, silica (SYLOPOL 948 manufactured by Grace Davison, Co., Ltd.) was dehydrated under vacuum at 400° C. for 15 h. 49.7 mL of a 10 wt % methylaluminoxane(MAO)/toluene solution was added to a glass reactor, and 9.1 g of silica (SYLOPOL 948 manufactured by Grace Davison, Co., Ltd.) was added thereto at 40° C., followed by agitation while raising the reactor temperature to 80° C. Thereafter, the temperature was maintained at 80° C., and 550 mg (0.1 mmol/g $SiO_2$) of the catalyst precursor prepared in Synthesis Example 1 was dissolved in 20 mL of toluene, and immediately added to the reactor. After agitation for 2 h, 948 mg (0.12 mmol/g $SiO_2$) of anilinium borate (N,N-dimethylanilinium tetrakis(pentafluorophenyl)borate, AB) previously dissolved in 20 mL of toluene was added in a solution state, followed by agitation at 40° C. for 2 h. After reaction was completed, agitation was stopped and a toluene layer was separated and removed. Remaining toluene was removed under reduced pressure at 40° C. to prepare a supported metallocene catalyst.

Comparative Examples 2 to 3: Preparation of Supported Metallocene Catalyst

Supported metallocene catalysts were prepared in the same manner as in Comparative Example 1, except that 465 mg (0.1 mmol/g $SiO_2$) of the catalyst precursor prepared in Synthesis Example 2 and 690 mg (0.1 mmol/g $SiO_2$) of the catalyst precursor prepared in Synthesis Example 3 were used, respectively, as shown in the following Table 1.

Comparative Example 4: Preparation of Supported Metallocene Catalyst

First, silica (SYLOPOL 948 manufactured by Grace Davison, Co., Ltd.) was dehydrated under vacuum at 400° C. for 15 h.

49.7 mL of 10 wt % methylaluminoxane(MAO)/toluene solution was added to a glass reactor, and 9.1 g of silica (SYLOPOL 948 manufactured by Grace Davison, Co., Ltd.) was added thereto at 40° C., followed by agitation while raising the reactor temperature to 80° C. Thereafter, the temperature was maintained at 80° C., and 520 mg (0.075 mmol/g $SiO_2$) of the catalyst precursor prepared in Synthesis Example 3 was dissolved in 20 mL of toluene, and added to the reactor, followed by agitation for 2 h. 550 mg (0.1 mmol/g $SiO_2$) of the catalyst precursor prepared in Synthesis Example 1 was reacted at 40° C. for 2 h. Then, 948 mg (0.12 mmol/g $SiO_2$) of anilinium borate (N,N-dimethylanilinium tetrakis(pentafluorophenyl)borate, AB) previously dissolved in 20 mL of toluene was added in a solution state, followed by agitation at 40° C. for 2 h. After reaction was completed, agitation was stopped and a toluene layer was separated and removed. Remaining toluene was removed under reduced pressure at 40° C. to prepare a supported metallocene catalyst.

<Slurry Polymerization ExamplePolymerization Example> Polymerization ExamplePolymerization Example 1

400 mL of hexane was added to an argon-filled closed system using a Parr reactor. Then, 1 g of trimethylaluminum was added to dry the inside of the reactor, and the hexane was discarded. The reactor was filled with 400 mL of hexane, and then 0.5 g of triisobutylaluminum was added thereto. 10 mg of the supported catalyst prepared in Example 1 was weighed in an argon-filled glove box, and added to the reactor. Then, argon was vented, and then polymerization was performed under ethylene pressure of 30 bar at 78° C. for 1 h.

Polymerization ExamplePolymerization Examples 2 to 12

Slurry polymerization was performed in the same manner as in Polymerization ExamplePolymerization Example 1, except that each of the supported catalysts prepared in Examples 2 to 12 was used, as shown in the following Table 1.

Comparative Polymerization ExamplePolymerization Examples 1 to 4

Slurry polymerization was performed in the same manner as in Polymerization ExamplePolymerization Example 1, except that each of the supported catalysts prepared in Comparative Examples 1 to 4 was used, as shown in the following Table 1.

Comparative Polymerization ExamplePolymerization Examples 5 to 8

Slurry polymerization was performed in the same manner as in Polymerization ExamplePolymerization Example 1, except that each of the supported catalysts prepared in Comparative Examples 1 to 4 was used, and 1.5 mg (0.6 mmol/g $SiO_2$) of the molecular weight modifier prepared in Synthesis Example 4 was further added to the reactor, as shown in the following Table 1.

Experimental Example

Experimental Example for Evaluation of Physical Properties of Polymers

Properties of the polyethylenes prepared in Polymerization ExamplePolymerization Examples 1 to 12 and Comparative Polymerization ExamplePolymerization Examples 1 to 4 were measured by the following methods, and the results are shown in the following Table 1.

a) Molecular weight (Mw): Molecular weight was determined as a weight average molecular weight by using gel permeation chromatography (GPC).

b) Molecular weight distribution (PDI): Molecular weight distribution was determined as a value obtained by dividing the weight average molecular weight by the number average molecular weight by using gel permeation chromatography (GPC).

c) Catalytic activity (Activity): 0.5 g of TMA was dried in a reactor, and about 100 mg of the supported catalyst was added to 400 mL of hexane, together with alkyl aluminum and the molecular weight modifier (MWE). Polymerization was performed at 80° C. under ethylene pressure of 9 bar for 1 h to obtain a polymer. The polymer was filtered and dried overnight, and then weighed to calculate the catalytic activity per unit time (h).

TABLE 1

| | Polymerization | Catalyst | Feed amount of MWE (mol %) | Activity (gPE/gCat/h) | Mw | PDI |
|---|---|---|---|---|---|---|
| Polymerization Example 1 | Supported catalyst slurry polymerization | Support/catalyst precursor 1/soluble MWE | 10* | 10.4 | 128,000 | 2.2 |
| Polymerization Example 2 | Supported catalyst slurry polymerization | Support/catalyst precursor 1/soluble MWE | 30* | 10.1 | 252,000 | 2.5 |
| Polymerization Example 3 | Supported catalyst slurry polymerization | Support/catalyst precursor 1/soluble MWE | 50* | 9.8 | 281,000 | 2.4 |
| Polymerization Example 4 | Supported catalyst slurry polymerization | Support/catalyst precursor 2/soluble MWE | 10* | 2.6 | 594,000 | 2.4 |
| Polymerization Example 5 | Supported catalyst slurry polymerization | Support/catalyst precursor 2/soluble MWE | 30* | 2.3 | 660,000 | 2.3 |
| Polymerization Example 6 | Supported catalyst slurry polymerization | Support/catalyst precursor 2/soluble MWE | 50* | 1.8 | 780,000 | 2.3 |
| Polymerization Example 7 | Supported catalyst slurry polymerization | Support/catalyst precursor 3/soluble MWE | 10* | 2.3 | 791,000 | 3.4 |
| Polymerization Example 8 | Supported catalyst slurry polymerization | Support/catalyst precursor 3/soluble MWE | 30* | 2.0 | 972,000 | 3.1 |
| Polymerization Example 9 | Supported catalyst slurry polymerization | Support/catalyst precursor 3/soluble MWE | 50* | 1.5 | 1,020,900 | 3.1 |
| Polymerization Example 10 | Supported catalyst slurry polymerization | Support/catalyst precursor 1(0.1) + 3(0.075)/soluble MWE | 10* | 11.6 | 273,000 | 3.4 |
| Polymerization Example 11 | Supported catalyst slurry polymerization | Support/catalyst precursor 1(0.1) + 3(0.075)/soluble MWE | 30* | 11.3 | 318,000 | 3.9 |
| Polymerization Example 12 | Supported catalyst slurry polymerization | Support/catalyst precursor 1(0.1) + 3(0.075)/soluble MWE | 50* | 11.5 | 298,000 | 3.3 |
| Comparative Polymerization Example 1 | Supported catalyst slurry polymerization | Support/catalyst precursor 1 | — | 10.1 | 103,100 | 2.1 |
| Comparative Polymerization Example 2 | Supported catalyst slurry polymerization | Support/catalyst precursor 2 | — | 2.8 | 553,000 | 2.5 |

TABLE 1-continued

|  | Polymerization | Catalyst | Feed amount of MWE (mol %) | Activity (gPE/gCat/h) | Mw | PDI |
|---|---|---|---|---|---|---|
| Comparative Polymerization Example 3 | Supported catalyst slurry polymerization | Support/catalyst precursor 3 | — | 2.3 | 693,000 | 3.6 |
| Comparative Polymerization Example 4 | Supported catalyst slurry polymerization | Support/catalyst precursor 1(0.1) + 3(0.075) | — | 11.1 | 263,000 | 3.6 |
| Comparative Polymerization Example 5 | Supported catalyst slurry polymerization | Support/catalyst precursor 1 | 600** | 6.3 | 228,000 | 2.2 |
| Comparative Polymerization Example 6 | Supported catalyst slurry polymerization | Support/catalyst precursor 2 | 600** | 1.3 | 710,000 | 2.3 |
| Comparative Polymerization Example 7 | Supported catalyst slurry polymerization | Support/catalyst precursor 3 | 600** | 1.0 | 730,000 | 3.4 |
| Comparative Polymerization Example 8 | Supported catalyst slurry polymerization | Support/catalyst precursor 1(0.1) + 3(0.075 | 600** | 7.3 | 293,000 | 3.2 |

Figure 2:
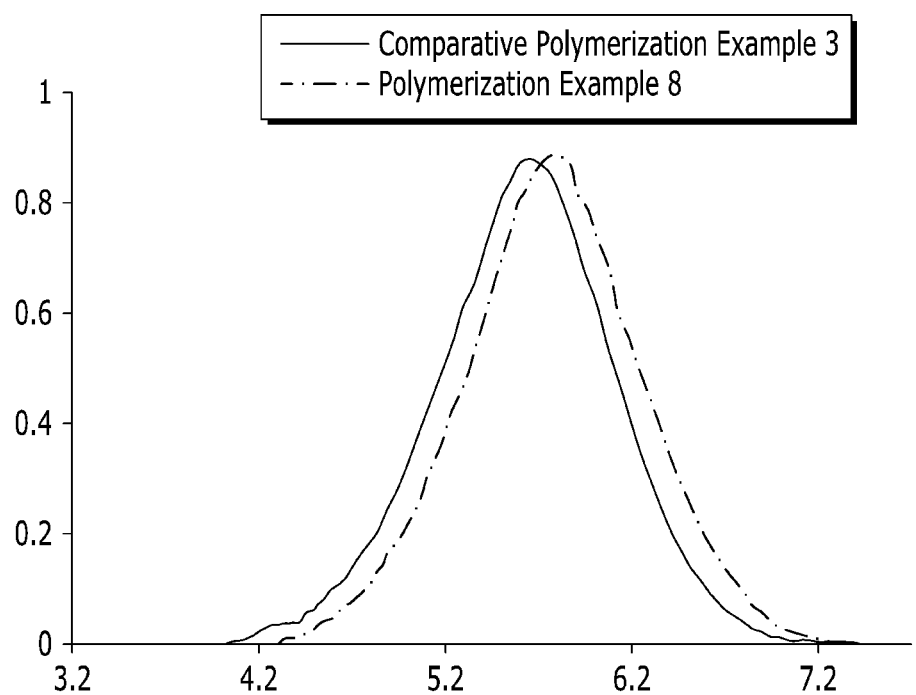
FIG. 2 is a graph showing molecular weight distributions of polymers which were polymerized by using supported metallocene catalysts prepared in Comparative Example 3 and Example 8 (red: Polymerization Example 8, green: Comparative Polymerization Example 3)
Figure 3:
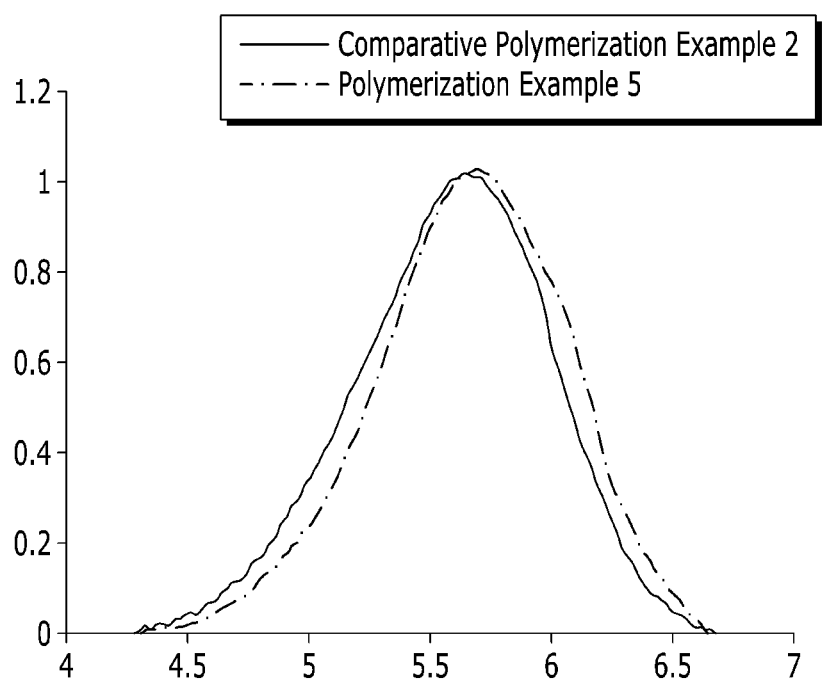
FIG. 3 is a graph showing molecular weight distributions of polymers which were polymerized by using supported metallocene catalysts prepared in Comparative Example 2 and Example 5 (red: Polymerization Example 5, blue: Comparative Polymerization Example 2).

*Polymerization Examples 1 to 12: the molecular weight modifier supported on the support was used.
**Comparative Polymerization Examples 5 to 8: soluble MWE as the molecular weight modifier was injected in an amount of 6 equivalent weights with respect to the precursor during the polymerization process Further, a graph showing molecular weight distributions of the polymers which were polymerized by using the supported metallocene catalysts prepared according to Examples 10 to 12 and Comparative Example 4 is shown in FIG. 1 (brown: Polymerization Example 10, red: Polymerization Example 11, purple: Polymerization Example 12, blue: Comparative Polymerization Example 4). A graph showing molecular weight distributions of the polymers which were polymerized by using the supported metallocene catalysts prepared according to Comparative Example 3 and Example 8 is shown in FIG. 2 (red: Polymerization Example 8, green: Comparative Polymerization Example 3). A graph showing molecular weight distributions of the polymers which were polymerized by using supported metallocene catalysts prepared in Comparative Example 2 and Example 5 is shown in FIG. 3 (red: Polymerization Example 5, blue: Comparative Polymerization Example 2). Here, the x axis represents dlogwf/dlogM and the y axis represents logM, and the vertical axis represents the intensity axis of the polymer and the horizontal axis represents the molecular weight axis of the polymer.

According to the graphs of the molecular weight distributions of the polymers, the present invention shows a little fluctuation in activity, compared to the prior technology. Also, it shows that the range of variation of the molecular weight depends on the amount of the modifier, indicating that the technology of the present invention enables fine control upon preparation of supported catalysts. Particularly, according to FIG. 2, when the existing molecular weight modifier was added during polymerization, the activity was greatly reduced and the molecular weight was not greatly increased. In contrast, when the catalyst was supported, increases of the molecular weight and activity were maintained to some degree. Further, as the molecular weight modifier varies, the peak of a molecular weight distribution graph moved toward the area of a high molecular weight polymer, and the shape of a molecular weight distribution graph is changed from a bimodal molecular weight distribution to a narrow unimodal molecular weight distribution. The shape of a narrow unimodal molecular weight distribution indicates that polymers having good physical properties were prepared, because the molecular weight distribution changes such that polymer elasticity being considered important in blow molding is increased to improve swell.

As shown in Table 1, the present invention may provide an effect of increasing a molecular weight of a polymer without a reduction in its activity or copolymerization property during olefin polymerization. Particularly, when an excessive amount of a molecular weight modifier is used, unreacted modifiers may enter a reactor again during a recovery process to cause a disruption of a polymerization, in some cases. In this case, an undesired polymerization process may occur to destabilize the process, and therefore injection of the molecular weight modifier into the reactor is not a commercially suitable method.

Moreover, as in Comparative Polymerization Examples 5 to 8, use of the molecular weight modifier during the polymerization process is not desirable in terms of reaction efficiency. In actual plants for mass-production, raw materials are reacted through recycling, and unreacted molecular weight modifiers unintentionally act on other reaction processes, resulting in undesired polymerization processes. That is, since the molecular weight modifier injected during the polymerization may cause instability in the entire polymerization process, it may cause instability in the actual large-scale system, even though the molecular weight control effect may be obtained at an experimental level. To solve these problems, in the present invention, the molecular weight modifier was used in a catalytic amount relative to the precursor, and thus the present invention is advantageous in that there are few side effects caused by the molecular weight modifier when actually applied to plants.

The invention claimed is:
1. A method of preparing a supported metallocene catalyst, comprising:
   preparing a molecular weight modifier composition by mixing a cyclopentadienyl metal compound of the following Chemical Formula 1 and an organic aluminum compound of the following Chemical Formula 2 and stirring a resulting mixture at room temperature for 50 hours to 108 hours; and
   supporting one or more metallocene compounds represented by any one of the following Chemical Formulae 3 to 6 and the molecular weight modifier composition on a support,
   wherein the molecular weight modifier composition is supported in an amount of about 1 mol % to 85 mol %, based on the total weight of the metallocene compound:

$$(R^1-Cp^1)(R^2-Cp^2)M^4X_2 \quad \text{Chemical Formula 1}$$

in Chemical Formula 1,
$Cp^1$ and $Cp^2$ are each independently a ligand comprising a cyclopentadienyl group, an indenyl group, or a fluorenyl group; $R^1$ and $R^2$ are substituents of $Cp^1$ and $Cp^2$, and are each independently hydrogen, an alkyl group having 1 to 20 carbon atoms, an alkenyl group having 1 to 20 carbon atoms, an alkylaryl group having 7 to 20 carbon atoms, an arylalkyl group having 7 to 20 carbon atoms, an aryl group having 6 to 20 carbon atoms, a heteroalkyl group having 1 to 20 carbon atoms, a heteroalkenyl group having 2 to 20 carbon atoms, a heteroalkylaryl group having 6 to 20 carbon atoms, a heteroarylalkyl group having 6 to 20 carbon atoms, or a heteroaryl group having 5 to 20 carbon atoms; $M^4$ is a Group 4 transition metal element; and X is a halogen, $$R^3R^4R^5Al \quad \text{Chemical Formula 2}$$

in Chemical Formula 2,
$R^3$, $R^4$, and $R^5$ are each independently an alkyl group having 4 to 20 carbon atoms or a halogen, and at least one of $R^3$, $R^4$, and $R^5$ is an alkyl group having 4 to 20 carbon atoms, $$(Cp^5R^a)_n(Cp^6R^b)M^1Z^1_{3-n} \quad \text{Chemical Formula 3}$$

in Chemical Formula 3,
$M^1$ is a Group 4 transition metal;
$Cp^5$ and $Cp^6$ are the same as or different from each other, and are each independenly any one selected from the group consisting of cyclopentadienyl, indenyl, 4,5,6,7-tetrahydro-1-indenyl, and fluorenyl radicals-which are optionally substituted with a hydrocarbon having 1 to 20 carbon atoms;
$R^a$ and $R^b$ are the same as or different from each other, and are each independently hydrogen, a C1 to C20 alkyl, a C1 to C10 alkoxy, a C2 to C20 alkoxyalkyl, a C6 to C20 aryl, a C6 to C10 aryloxy, a C2 to C20 alkenyl, a C7 to C40 alkylaryl, a C7 to C40 arylalkyl, a C8 to C40 arylalkenyl, or a C2 to C10 alkynyl;
$Z^1$ is a halogen atom, a C1 to C20 alkyl, a C2 to C10 alkenyl, a C7 to C40 alkylaryl, a C7 to C40 arylalkyl, a C6 to C20 aryl, a substituted or unsubstituted C1 to C20 alkylidene, a substituted or unsubstituted amino group, a C2 to C20 alkylalkoxy, or a C7 to C40 arylalkoxy; and
n is 1 or 0, $$(Cp^7R^c)_mB^1(Cp^8R^d)M^2Z^2_{3-m} \quad \text{Chemical Formula 4}$$

in Chemical Formula 4,
$M^2$ is a Group 4 transition metal;
$Cp^7$ and $Cp^8$ are the same as or different from each other, and are each independently any one selected from the group consisting of cyclopentadienyl, indenyl, 4,5,6,7-tetrahydro-1-indenyl, and fluorenyl radicals, and these are substituted with a hydrocarbon having 1 to 20 carbon atoms;
$R^c$ and $R^d$ are the same as or different from each other, and are each independently hydrogen, a C1 to C20 alkyl, a C1 to C10 alkoxy, a C2 to C20 alkoxyalkyl, a C6 to C20 aryl, a C6 to C10 aryloxy, a C2 to C20 alkenyl, a C7 to C40 alkylaryl, a C7 to C40 arylalkyl, a C8 to C40 arylalkenyl, or a C2 to C10 alkynyl;
$Z^2$ is a halogen atom, a C1 to C20 alkyl, a C2 to C10 alkenyl, a C7 to C40 alkylaryl, a C7 to C40 arylalkyl, a C6 to C20 aryl, a substituted or unsubstituted C1 to C20 alkylidene, a substituted or unsubstituted amino group, a C2 to C20 alkylalkoxy, or a C7 to C40 arylalkoxy;
$B^1$ is any one or more of carbon, germanium, silicon, phosphorus, or nitrogen atom-containing radicals, which crosslink a $Cp^3R^c$ ring and a $Cp^4R^d$ ring or crosslink one $Cp^4R^d$ ring to $M^2$, or a combination thereof; and
m is 1 or 0, $$(Cp^9R^e)B^2(J)M^3Z^3_2 \quad \text{Chemical Formula 5}$$

in Chemical Formula 5,
$M^3$ is a Group 4 transition metal;
$Cp^9$ is any one selected from the group consisting of cyclopentadienyl, indenyl, 4,5,6,7-tetrahydro-1-indenyl, and fluorenyl radicals, and these are substituted with a hydrocarbon having 1 to 20 carbon atoms;
$R^e$ is hydrogen, a C1 to C20 alkyl, a C1 to C10 alkoxy, a C2 to C20 alkoxyalkyl, a C6 to C20 aryl, a C6 to C10 aryloxy, a C2 to C20 alkenyl, a C7 to C40 alkylaryl, a C7 to C40 arylalkyl, a C8 to C40 arylalkenyl, or a C2 to C10 alkynyl;
$Z^3$ is a halogen atom, a C1 to C20 alkyl, a C2 to C10 alkenyl, a C7 to C40 alkylaryl, a C7 to C40 arylalkyl, a C6 to C20 aryl, a substituted or unsubstituted C1 to C20 alkylidene, a substituted or unsubstituted amino group, a C2 to C20 alkylalkoxy, or a C7 to C40 arylalkoxy;
$B^2$ is any one or more of carbon, germanium, silicon, phosphorus, or nitrogen atom-containing radicals, which crosslink a $Cp^5R^e$ ring to J, or a combination thereof;
J is any one selected from the group consisting of $NR^f$, O, $PR^f$ and S; and $R^f$ is a C1 to C20 alkyl, aryl, substituted alkyl, or substituted aryl,

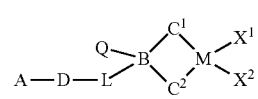

Chemical Formula 6 in Chemical Formula 6,
A is hydrogen, a halogen, a C1 to C20 alkyl group, a C2 to C20 alkenyl group, a C6 to C20 aryl group, a C7 to C20 alkylaryl group, a C7 to C20 arylalkyl group, a C1 to C20 alkoxy group, a C2 to C20 alkoxyalkyl group, a C3 to C20 heterocycloalkyl group, or a C5 to C20 heteroaryl group;
D is —O—, —S—, —N(R)—, or —Si(R)(R')—, in which R and R' are the same as or different from each other, and are each independently hydrogen, a halogen, a C1 to C20 alkyl group, a C2 to C20 alkenyl group, or a C6 to C20 aryl group;

L is a C1 to C10 straight or branched alkylene group;

B is carbon, silicon, or germanium;

Q is hydrogen, a halogen, a C1 to C20 alkyl group, a C2 to C20 alkenyl group, a C6 to C20 aryl group, a C7 to C20 alkylaryl group, or a C7 to C20 arylalkyl group;

M is a Group 4 transition metal;

$X^1$ and $X^2$ are the same as or different from each other, and are each independently a halogen, a C1 to C20 alkyl group, a C2 to C20 alkenyl group, a C6 to C20 aryl group, a nitro group, an amido group, a C1 to C20 alkylsilyl group, a C1 to C20 alkoxy group, or a C1 to C20 sulfonate group;

$C^1$ and $C^2$ are the same as or different from each other, and are each independently represented by any one of the following Chemical Formula 7a, Chemical Formula 7b, and Chemical Formula 7c, excluding that both $C^1$ and $C^2$ are Chemical Formula 7c,

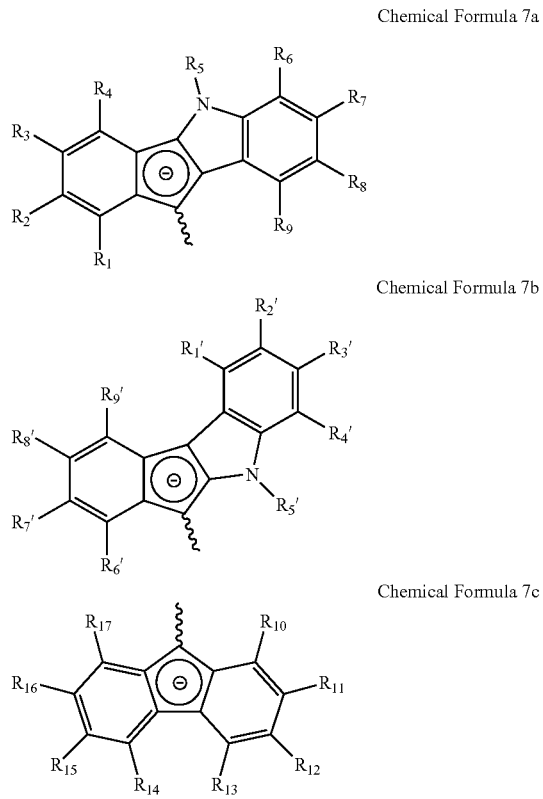

Chemical Formula 7a

Chemical Formula 7b

Chemical Formula 7c in Chemical Formulae 7a, 7b, and 7c, $R_1$ to $R_{17}$ and $R_1'$ to $R_9'$ are the same as or different from each other, and are each independently hydrogen, a halogen, a C1 to C20 alkyl group, a C2 to C20 alkenyl group, a C1 to C20 alkylsilyl group, a C1 to C20 silylalkyl group, a C1 to C20 alkoxysilyl group, a C1 to C20 alkoxy group, a C6 to C20 aryl group, a C7 to C20 alkylaryl group, or a C7 to C20 arylalkyl group, and two or more neighboring groups of $R_{10}$ to $R_{17}$ are connected to each other to form a substituted or unsubstituted aliphatic or aromatic ring.

2. The method of preparing the supported metallocene catalyst of claim 1, wherein the supporting is performed by mixing the support, the metallocene catalyst, and the molecular weight modifier composition, and stirring a resulting mixture at a temperature of 30° C. to 100° C. for 1 hour to 12 hours.

3. The method of preparing the supported metallocene catalyst of claim 1, wherein $R^1$ and $R^2$ in Chemical Formula 1 are each independently selected from the group consisting of hydrogen, methyl, ethyl, butyl, and t-butoxy hexyl.

4. The method of preparing the supported metallocene catalyst of claim 1, wherein $R^3$, $R^4$, and $R^5$ in Chemical Formula 2 are each independently an isobutyl group.

5. The method of preparing the supported metallocene catalyst of claim 1, wherein $M^4$ in Chemical Formula 1 is selected from the group consisting of titanium, zirconium, and hafnium.

6. The method of preparing the supported metallocene catalyst of claim 1, wherein the molecular weight modifier composition comprises a compound represented by the following Chemical Formula 8, Chemical Formula 9, Chemical Formula 10, or Chemical Formula 11:

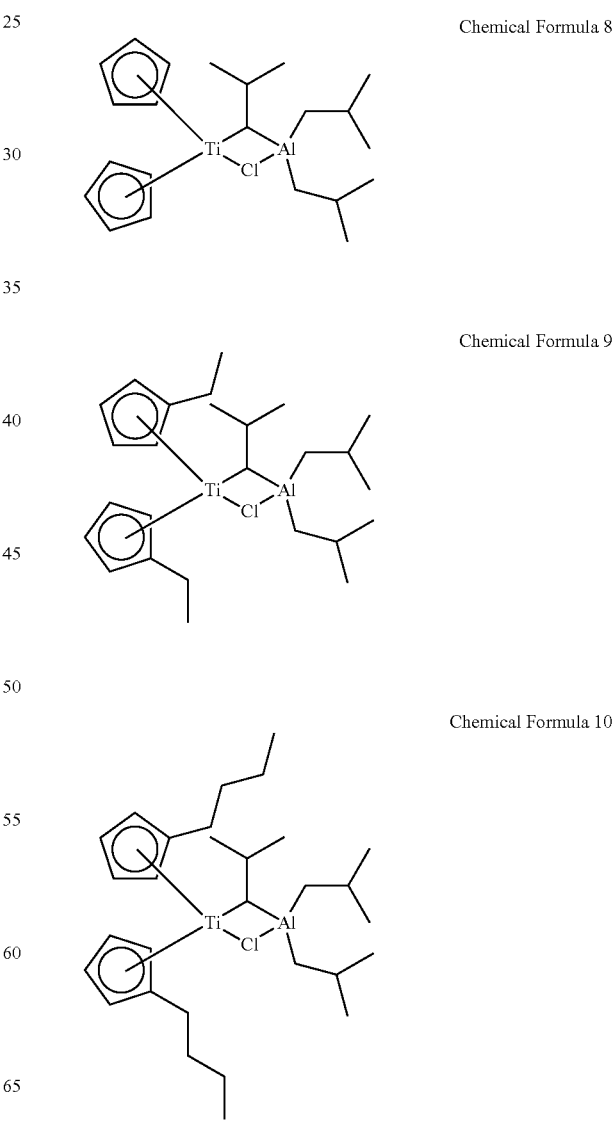

Chemical Formula 8

Chemical Formula 9

Chemical Formula 10

Chemical Formula 11

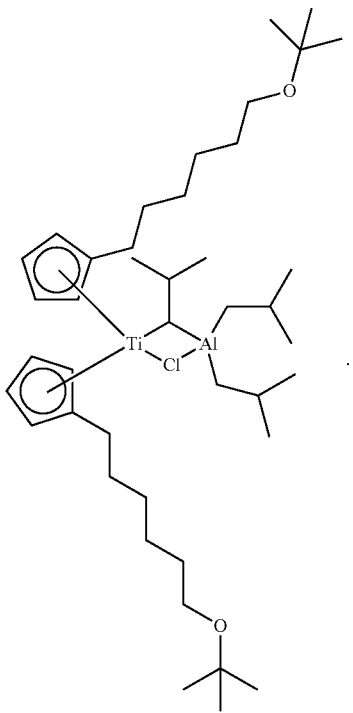

7. The method of preparing the supported metallocene catalyst of claim 1, wherein the support is selected from the group consisting of silica, silica-alumina, and silica-magnesia.

8. The method of preparing the supported metallocene catalyst of claim 1, wherein the support is one on which a first aluminum-containing cocatalyst of the following Chemical Formula 12 is supported:

-[-Al($R^{18}$)—O-]$_n$-         Chemical Formula 12 in Chemical Formula 12,
each $R^{18}$ is independently a halogen, or a halogen-substituted or unsubstituted hydrocarbyl having 1 to 20 carbon atoms, and n is an integer of 2 or more.

9. The method of preparing the supported metallocene catalyst of claim 8, wherein the molecular weight modifier composition is supported immediately after supporting the metallocene compound onto the first cocatalyst-supported support.

10. The method of preparing the supported metallocene catalyst of claim 1, wherein a second borate-based cocatalyst of the following Chemical Formula 13 is further supported:

$T^+[BQ_4]^-$         Chemical Formula 13 in Chemical Formula 13,
$T^+$ is a positive monovalent (+1) polyatomic ion, B is boron having an oxidation state of +3, each Q is independently selected from the group consisting of a hydride group, a dialkylamido group, a halide group, an alkoxide group, an aryloxide group, a hydrocarbyl group, a halocarbyl group, and a halo-substituted hydrocarbyl group, in which Q has 20 or fewer carbon atoms, provided that only one or fewer of Q is a halide group.

11. A method of preparing a polyolefin, comprising polymerizing olefinic monomers in the presence of the supported metallocene catalyst prepared according to claim 1.

12. The method of preparing the polyolefin of claim 11, wherein the polymerizing of olefinic monomers is performed by slurry polymerization of olefinic monomers in the presence of a supported metallocene catalyst which is obtained by supporting a metallocene compound on a support, together with a molecular weight modifier composition comprising a reaction product of a cyclopentadienyl metal compound and an organic aluminum compound.

13. The method of preparing the polyolefin of claim 11, wherein the olefinic monomer comprises one or more monomers selected from the group consisting of ethylene, propylene, 1-butene, 1-pentene, 4-methyl-1-pentene, 1-hexene, 1-heptene, 1-octene, 1-decene, 1-undencene, 1-dodecene, 1-tetradecene, 1-hexadecene, 1-eicosene, norbornene, norbornadiene, ethylidenenorbornene, phenylnorbornene, vinylnorbornene, dicyclopentadiene, 1,4-butadiene, 1,5-pentadiene, 1,6-hexadiene, styrene, alpha-methylstyrene, divinylbenzene, and 3-chloromethylstyrene.

* * * * *